US011173233B2

(12) United States Patent
Van Dyke

(10) Patent No.: US 11,173,233 B2
(45) Date of Patent: *Nov. 16, 2021

(54) KERATIN BIOCERAMIC COMPOSITIONS

(71) Applicant: Wake Forest University Health Sciences, Winston-Salem, NC (US)

(72) Inventor: Mark E. Van Dyke, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 184 days.

This patent is subject to a terminal disclaimer.

(21) Appl. No.: 14/547,839

(22) Filed: Nov. 19, 2014

(65) Prior Publication Data

US 2015/0141333 A1 May 21, 2015

Related U.S. Application Data

(63) Continuation of application No. 11/549,748, filed on Oct. 16, 2006, now Pat. No. 8,920,827.

(60) Provisional application No. 60/728,971, filed on Oct. 21, 2005.

(51) Int. Cl.
| | |
|---|---|
| *A61L 27/42* | (2006.01) |
| *A61L 27/54* | (2006.01) |
| *A61L 27/58* | (2006.01) |

(52) U.S. Cl.
CPC .............. *A61L 27/54* (2013.01); *A61L 27/425* (2013.01); *A61L 27/58* (2013.01); *A61L 2300/406* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,434,688 A | 1/1948 | Evans | |
| 2,445,028 A | 7/1948 | Jones et al. | |
| 2,517,572 A | 8/1950 | Jones et al. | |
| 2,814,851 A | 12/1957 | Hervey | |
| 3,033,755 A | 5/1962 | Jacobi | |
| 3,642,498 A | 2/1972 | Anker | |
| 3,655,416 A | 4/1972 | Vinson et al. | |
| 4,178,361 A | 12/1979 | Cohen et al. | |
| 4,357,274 A | 11/1982 | Werner et al. | |
| 4,423,032 A | 12/1983 | Abe et al. | |
| 4,495,173 A | 1/1985 | Matsunaga et al. | |
| 4,570,629 A | 2/1986 | Widra | |
| 4,751,074 A | 6/1988 | Matsunaga et al. | |
| 4,774,227 A | 9/1988 | Piez et al. | |
| 4,795,467 A | 1/1989 | Piez et al. | |
| 4,865,602 A | 9/1989 | Smestad et al. | |
| 4,895,722 A | 1/1990 | Abe et al. | |
| 4,959,213 A | 9/1990 | Brod et al. | |
| 5,047,249 A | 9/1991 | Rothman et al. | |
| 5,300,285 A | 4/1994 | Halloran et al. | |
| 5,320,796 A | 6/1994 | Harashima et al. | |
| 5,358,935 A | 10/1994 | Smith et al. | |
| 5,634,945 A | 6/1997 | Pernia et al. | |
| 5,636,643 A | 6/1997 | Argenta et al. | |
| 5,645,081 A | 7/1997 | Argenta et al. | |
| 5,651,966 A | 7/1997 | Read et al. | |
| 5,679,819 A | 10/1997 | Jones et al. | |
| 5,763,583 A | 6/1998 | Arai et al. | |
| 5,883,078 A | 3/1999 | Seelich et al. | |
| 5,902,608 A | 5/1999 | Read et al. | |
| 5,932,552 A | 8/1999 | Blanchard et al. | |
| 5,948,432 A | 9/1999 | Timmons et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,165,496 A | 12/2000 | Timmons et al. | |
| 6,268,454 B1 | 7/2001 | Song et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,274,163 B1 | 8/2001 | Blanchard et al. | |
| 6,309,422 B1 | 10/2001 | Farrington et al. | |
| 6,316,598 B1 | 11/2001 | Van Dyke et al. | |
| 6,371,984 B1 | 4/2002 | Van Dyke et al. | |

(Continued)

FOREIGN PATENT DOCUMENTS

| | | |
|---|---|---|
| DE | 184915 | 12/1905 |
| DE | 22643 | 10/1907 |

(Continued)

OTHER PUBLICATIONS

Kenley et al., Biotechnology and bone graft substitutes, Pharm Res. Oct. 1993;10(10):1393-401, printed from http://www.ncbi.nlm.nih.gov/pubmed/8272399, 2 pages.*

Alexander, P.; Earland, C.; "Structure of wool fibers—Isolation of an α and β-protein in wool." Nature; vol. 166, 1950.

Almog, J.; et al; "Reversible binding of dioxygen to mesoporphyrin IX derivatives at low temperatures."; Journal of the American Chemical Society; vol. 96(17), 1974, pp. 5600-5601.

Almog, J.; et al; "Reversible oxygenation and autoxidation of a capped porphyrin iron (II) complex."; Journal of the American Chemical Society; vol. 97(1), 1975, pp. 227-228.

Alvis, MR, et al., NeuColl, Inc., Palo Alto, CA, Successful Induction of New Bone Formation by Collagraft (Mar. 12-15, 2000) 46th Annual Meeting of the Orthopaedic Research Society, Orlando, FL.

Amiya, T.; et al;"Conformational studies of the α-helical proteins from wool keratins by c.d." International Journal of Biological Macromolecules; vol. 4, 1982, pp. 165-172.

(Continued)

*Primary Examiner* — Gigi G Huang
(74) *Attorney, Agent, or Firm* — Myers Bigel, P.A.

(57) ABSTRACT

A malleable bone graft composition is described. The composition comprises: (a) keratose; (b) particulate filler; (c) antibiotic; and (d) water. The invention may be provided in sterile form in an container, and optionally lyophilized. Methods of treating a fracture with such compositions are also described.

17 Claims, 7 Drawing Sheets

(56) References Cited

U.S. PATENT DOCUMENTS

| | | | |
|---|---|---|---|
| 6,379,690 B2 | 4/2002 | Blanchard et al. | |
| 6,432,435 B1 | 8/2002 | Timmons et al. | |
| 6,461,628 B1 | 10/2002 | Blanchard et al. | |
| 6,544,548 B1 | 4/2003 | Siller-Jackson et al. | |
| 6,696,073 B2 | 2/2004 | Boyce et al. | |
| 6,746,836 B1 | 6/2004 | Widra | |
| 6,783,546 B2 | 8/2004 | Zucherman et al. | |
| 6,825,323 B2 | 11/2004 | Hess | |
| 6,833,488 B2 | 12/2004 | Bucevschi et al. | |
| 6,869,445 B1 | 3/2005 | Johnson | |
| 7,297,342 B2 | 11/2007 | Peplow et al. | |
| 7,439,012 B2 | 10/2008 | Van Dyke | |
| 7,892,572 B2 | 2/2011 | Peplow et al. | |
| 7,892,573 B2 | 2/2011 | Van Dyke | |
| 8,299,013 B2 | 10/2012 | Van Dyke | |
| 8,920,827 B2 * | 12/2014 | Dyke | A61L 27/425 424/423 |
| 2001/0018614 A1 * | 8/2001 | Bianchi | A61F 2/28 623/16.11 |
| 2002/0187104 A1 * | 12/2002 | Li | A61K 38/02 424/44 |
| 2002/0192196 A1 | 12/2002 | Allen-Hoffmann | |
| 2003/0109587 A1 | 6/2003 | Mori | |
| 2003/0228353 A1 | 12/2003 | Cowsar | |
| 2004/0033949 A1 * | 2/2004 | Bunting | A61K 9/0024 514/8.1 |
| 2004/0062793 A1 | 4/2004 | Dyke | |
| 2004/0078090 A1 | 4/2004 | Binette et al. | |
| 2004/0120910 A1 | 6/2004 | Dyke | |
| 2004/0267362 A1 | 12/2004 | Hwang et al. | |
| 2005/0084542 A1 | 4/2005 | Rosenberg et al. | |
| 2007/0166348 A1 | 7/2007 | Van Dyke | |
| 2008/0274165 A1 | 11/2008 | Van Dyke | |
| 2009/0004242 A1 | 1/2009 | Van Dyke | |
| 2009/0017001 A1 | 1/2009 | Van Dyke | |
| 2009/0047260 A1 | 2/2009 | Van Dyke | |

FOREIGN PATENT DOCUMENTS

| | | |
|---|---|---|
| EP | 0089152 A1 | 9/1983 |
| EP | 0 454 600 A1 | 4/1991 |
| EP | 0468797 A2 | 1/1992 |
| EP | 0 540 357 A2 | 5/1993 |
| GB | 531446 A | 1/1941 |
| GB | 2 241 253 A | 8/1991 |
| JP | 52-148581 A | 12/1977 |
| JP | 53-016091 A | 2/1978 |
| JP | 54-137064 A | 10/1979 |
| JP | 55-051095 A | 4/1980 |
| JP | 56-030909 A | 3/1981 |
| JP | 55-98256 | 2/1982 |
| JP | S57-109797 | 7/1982 |
| JP | 60-122568 A | 7/1985 |
| JP | 1-174528 | 7/1989 |
| JP | 2-051533 A | 2/1990 |
| JP | 3-011099 A | 1/1991 |
| JP | 4-082561 A | 3/1992 |
| JP | 4-091138 A | 3/1992 |
| JP | 4-189833 | 7/1992 |
| JP | 5-285374 A | 11/1993 |
| JP | 5-285375 A | 11/1993 |
| JP | 5-320358 A | 12/1993 |
| JP | 6-100600 A | 4/1994 |
| JP | 6-116300 A | 4/1994 |
| JP | 6-336499 A | 12/1994 |
| JP | 8332087 A | 12/1996 |
| JP | 9-227565 A | 9/1997 |
| JP | 10-291998 A | 11/1998 |
| JP | 10-291999 A | 11/1998 |
| JP | 10-337466 | 12/1998 |
| JP | 2000-191792 A | 7/2000 |
| JP | 2001-087754 A | 4/2001 |
| JP | 2001-114647 A | 4/2001 |
| JP | 2001329183 A | 11/2001 |
| JP | 2004136096 A | 5/2004 |
| NL | 51000577 | 12/1941 |
| RU | 2 106 154 C1 | 3/1998 |
| RU | 2 108 079 C1 | 4/1998 |
| WO | WO 91-02538 A1 | 3/1991 |
| WO | WO 93/10827 A1 | 6/1993 |
| WO | WO 93/12819 A1 | 7/1993 |
| WO | WO 98/08550 A1 | 3/1998 |
| WO | WO 99/26570 A1 | 6/1999 |
| WO | WO 99/26595 A1 | 6/1999 |
| WO | WO 99/51175 A1 | 10/1999 |
| WO | WO 00/76437 A1 | 12/2000 |
| WO | WO 01/19283 A2 | 3/2001 |
| WO | WO 01/19305 A1 | 3/2001 |
| WO | WO 01/64033 A2 | 9/2001 |
| WO | WO 02/45508 A1 | 6/2002 |
| WO | WO 03/011894 A1 | 2/2003 |
| WO | WO 03/064449 A2 | 8/2003 |
| WO | WO 03/086491 A2 | 10/2003 |
| WO | WO 2004/091432 A2 | 10/2004 |
| WO | WO 2007/098053 | 8/2007 |

OTHER PUBLICATIONS

Ando, H.; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.

Ashkenasy, G.; et al; "Assemblies of "hinged" iron-porphyrins as potential oxygen sensors."; Journal of the American Chemical Society; vol. 122, No. 6, 2000, pp. 1116-1122.

Baldwin, J.E.; et al; "Binding of dioxygen to iron (II), Reversible behavior in solution."; Journal of the American Chemical Society; vol. 95 (17), 1973, pp. 5757-5759.

Barr, M.; "Oxidation, reduction and hydroysis of wool keratin."; Iowa State Coll. Journal of Science, vol. 12, 1937, pp. 106-107, Abstract Only.

Bawden, C.S.; et al; "Expression of bacterial cysteine biosynthesis genes in transgenic mice and sheep: toward a new in vivo acid biosynthesis pathway and improved wool growth." Transgenic Research; vol. 4, 1995, pp. 87-104.

Bawden, C.S.; et al; "Expression of wool intermediate filament keratin transgene in sheep fibre alters structure."; Transgenic Research; vol. 7, 1998, pp. 273-287.

Bawden, C.S.; et al; "Improvement of wool quality by transgenesis."; Science Update, Conf: OECD, 2001, pp. 67-76, Abstract Only.

Bawden, C.S.; et al; "Sheep transgenesis with keratin and non-keratin genes: expression in the wool follicle for the modified fibre properties and growth rates."; Experimental Dermatology; vol. 8, 1999, pp. 342-343.

Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.

Besse, D.; et al; "Synthesis of selenocysteine peptides and their oxidation to diselenide-bridged compounds."; Journal of Peptide Science; vol. 3 (6), 1997, pp. 442-453.

Bettex-Galland, M. et al.; "Advances in Protein Chemistry." Academic Press, vol. 20, 1965.

Bhatnagar, G.M. et al; "Difference sprectra of kerateine-B."; International Journal of Protein Research; vol. 1 No. 3, 1969, pp. 213-219.

Bhatnagar, G.M.; et al;"Assessment of confirmational changes in low-sulfur S-(carboxymethyl)keratin from wool."; Australian Journal of Biological Sciences; vol. 20, No. 4, 1967, pp. 827-836, Abstract Only.

Bhatnagar, G.M.; et al; "The conformation of the high sulphur proteins of wool. I The preparation and properties of a water soluble metakeratin."; International Journal of Protein Research; vol. 1 (3), 1969, pp. 199-212.

Bhatnagar, G.M.; et al; "The conformation of the high-sulphur proteins of wool. II—Difference spectra of kerateine-B." International Journal of Protein Research I; 1969, pp. 213-219.

(56) References Cited

OTHER PUBLICATIONS

Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.

Blessing, M.; et al.; "Transgenic mice as a model to study the role of TGF-β-related molecules in hair follicles." Genes and Development; vol. 7, 1993, pp. 204-215.

Bradbury, J.H.; "The structure and chemistry of keratin fibers." Advanced Protein Chemistry; vol. 27, 1973, pp. 111-211.

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histiological components of keratin fibers and analyses of cuticles."; Nature; vol. 210, No. 5043, 1966, pp. 1333-1334.

Breinl, F.; et al; "The oxidative breaking up of keratin through treatment with hydrogen peroxide." Z.Physiol. Chemistry; vol. 52, 1907, pp. 158-169, Abstract Only.

Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.

Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.

Brunner, H.; Brunner, A.;"Fractionation of tyrosine-rich proteins from oxidized wool by ion-exchange chromotography and preparative electrophoresis."; European Journal Biochemistry; vol. 32, 1973, pp. 350-355.

Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260, Abstract Only.

Cameron, J.H.; et al; "Nickel (II) and cobalt (II) complexes of potentially quinquedentate macrobicyclic ligands. Reversible binding to dioxygen to a cobalt (II) complex."; Journal of the Chemical Society, Dalton Transactions: Inorganic Chemistry; vol. 3, 1993, pp. 397-402.

Campbell, M.E.; Whiteley, K.J.; Gillespie, J.M.; "Compositional studies of high and low-crimp wools."; Australian Journal of Biological Sciences; vol. 25, 1972, pp. 977-987.

Carey, J.R.; et al; "Design and synthesis of novel metalloproteins through reversible encapsulation of metal complexes by proteins." Abstract of Papers, 222nd ACS National Meeting, 2001, Abstract Only.

Chatani, E.; et al.; "A film formation technology of wool keratin."; Textile and Fashion; vol. 14(5), 1997, pp. 227-235, Abstract Only.

Chatani, E.; et al; "Research on merchandizing technology of wool keratin. Film formation technology of wool keratin."; Owari Textile Research Annual Report No. 93, 1998, pp. 93-101, Abstract Only.

Clark, R.A.F. Editor; "The Molecular and Cellular Biology of Wound Repair."; Plenum Press 2nd Edition, 1996, 1988, pp. 3-51, 168-309.

Cornell, CN, Long-Term Results Associated with the Use of Collagen-Calcium Phosphate (Collagraft®) as a Bone Graft Substitute in Fractures and Non-Unions of the Humeral Shaft (Oct. 18-20, 2001) Orthopaedic Trauma Association Annual Meeting, San Diego, CA.

Crewther WG et al., The Chemistry of Keratins. Anfinsen CB Jr et al., editors. Advances in Protein Chemistry (1965) Academic Press. New York:191-346.

Crewther, W.G. et al; "Helix-rich fraction from the low-sulphur proteins of wool."; Nature; vol. 207,(4994), 1965, p. 295.

Crewther, W.G.; Effect of aftertreatment on the stability of set wool fibers. Comments; Journal of the Society of Dyers and Colourist; vol. 86, No. 5, 1970, p. 208, Abstract Only.

Crewther, W.G.;"The concept of internal pH in wool fibers and the interpretation of data relating to setting."; Journal of the Society of Dyers and Colourist; vol. 81, (4), 1965, pp. 156-158, Abstract Only.

Crewther, W.G.; "The viscoelasticity of alpha keratin fibers."; Experimental Dermatology; vol. 8 (4), 1999, pp. 343-344.

Crewther, W.G.; "Preparation and properties of large peptides from the helical regiones of the low-sulfur proteins of wool."; Applied Polymer Symposia; vol. 18, No. 1, 1971, pp. 1-20, Abstract Only.

Crewther, W.G.; "Structure of .alpha-keratin."; Textile Research Journal; vol. 42, No. 4, 1972, pp. 251-252.

Crewther, W.G.; "The stress-strain characteristics of animal fibers after reduction and alkylation."; Textile Research Journal; vol. 35, No. 10, 1965, pp. 867-877.

Crewther, W.G.; "Thiol-disulfide interchange reactions in the setting of single wool fibers." Journal of the Society of Dyers and Colourist; vol. 82, No. 1, 1966, pp. 54-58 , Abstract Only.

Crewther, W.G.; at al; "Effect of S-carboxymethylation of wool proteins on the iodination of tyrosine residues."; Textile Research Journal; vol. 41, No. 3, 1971, 99.267.

Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.

Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.

Crewther, W.G.; et al.; "Amino acid sequences of α-helical segments from S-carboxymethlykerateine-A. Tryptic and chymotryptic peptides from a type-II segment."; Biochemistry Journal; vol. 173, 1978 pp. 353-363.

Crewther, W.G.; et al; "Formation of various crosslinkages in wool and their effect on the supercontraction properties of the fibers."; Textile Research Journal; vol. 37, No. 9, 1967, pp. 736-745.

Crewther, W.G.; et al; "Low-sulfur proteins from α-keratins. Interrelationship between their amino acid compositions, α-helix contents, and the supercontraction of the parent keratin." Biopolymers, vol. 4, 1966, pp. 905-916.

Crewther, W.G.; et al; "Reduction of S-carboxymethlycysteine and methionine with sodium in liquid ammonia." Biochimica et Biophysica Acta; vol. 164, 1969, pp. 606-609.

Crewther, W.G.; et al; "Structure of intermediate filaments."; International Journal of Biological Macrmolecules; vol. 5, No. 5, 1983, pp. 267-274, Abstract Only.

Crewther, W.G.; et al; "The chemistry of keratins."; Advance Protein Chemistry; vol. 20, 1965 pp. 191-346.

Crewther, W.G.; et al; "The preparation and properties of a helix-rich fraction obtained by partial proteolysis of low sulfur S-Carboxymethylkerateine from wool." The Journal of Biological Chemistry; vol. 242, No. 19, 1967, pp. 4310-4319.

Dale, H.N.; "Keratin and other coatings for pills."; Pharmacology Journal; vol. 129, 1932, pp. 494-495, Abstract Only.

Damaglou, A.P.; et al; "The hydrolysis by thermolysin of dipeptide derivatives that contain substituted cysteine" Biochemical Journal; vol. 123, No. 3, 1971, pp. 379-384.

Darskus, R.L.; et al.; "Breed and species differences in the hair proteins of four genera of caprini." Australian Journal of Biological Sciences; vol. 24, 1971, pp. 515-524.

Darskus, R.L.; et al; "The possibility of common amino acid sequences in high sulphur protein fractions from wool." Australian Journal of Biological Sciences; vol. 22, 1969, pp. 1197-1204.

De Sanctis, G.; et al;"Mini-myoglobin—Electron paramagnetic resonance and reversible oxygenation of the cobalt derivative."; Journal of Molecular Biology; vol. 222, 1991, pp. 637-643.

Dedeurwaerder, R.A.; et al; "Selective extraction of protein fraction from wool keratin." Nature vol. 203, 1964, pp. 48,49.

Dobb, M.G.; et al; "Electron microscopy of fibrous keratins."; Symposuim of fibrous protein, Int Conf.; 1967, pp. 267-278, Abstract Only.

Dowling, L.M.; Crewther, W.G.; Inglis, A.S.;"The primary structure of component 8c-1, a subunit protein of intermediate filaments in wool keratin."; Biochemistry Journal vol. 236, 1986, pp. 695-703.

(56) References Cited

OTHER PUBLICATIONS

Dowling, L.M.; Crewther, W.G.; Parry, D.A.D.;"The secondary structure of component 8c-1, of alpha-keratin."; Biochemistry Journal; vol. 236, 1986, pp. 705-712.
Dowling, L.M.; et al; "Effect of the solvent on the iodanation of a tyrosine derivative and its relation to iodination of wool."; Textile Research Journal; vol. 41, No. 1, 1971, pp. 65-69.
Dowling, L.M.; et al; "Isolation of components from the low sulphur proteins of wool by fractional precipitation."; Preparative Biochemistry, vol. 4(3), 1974, pp. 203-226.
Downes, A.M.; et al;"Evaluation of modified [35S] methionine and [35S] casein preparations as supplements for sheep"; British Journal of Nutrition; vol. 24, No. 4, 1970, pp. 1083-1089.
Downes, A.M.; et al; "Matabolic fate of parenterally administered sulphur containing amino acids in sheep and the effects on growth and composition of wool"; Australian Journal of Biological Sciences; vol. 23, No. 5, 1970, pp. 1077-1088.
Downes, A.M.; Ferguson,K.A.; Gillespie, J.M.; Harrap, B.S.; "A study of the proteins of the wool follicle." Australian Journal of Biological Science; vol. 19. 1966, pp. 319-333.
Dunn, S.M.; et al; "Regulation of hair gene expression."; Experimental Dermatology, vol. 8, 1999, pp. 341-342.
Earland, C.; et al; "Structure of keratin. II. Amino acid content of fractions isolated from oxidized wool."; Biochimica et Biophysica Acta; vol. 22, 1956, pp. 405-411.
Ebright, Y.W.; et al.; "N-(lodoacetyl)-p-phenylenediamine-EDTA: A regent for high-efficiency incorporation of an EDTA-metal complex at a rationally selected site within a protein."; Bioconjugate Chemistry; vol. 4 (3), 1993, pp. 219-225.
Edwards, B.; et al; "Chemical studies on powdered keratins." Journal of Biological Chemistry; vol. 154, 1944, pp. 593-596.
Elleman, T.C.; et al; Amino acid sequences of alpha-helical segments from S-carboxymethylkerateine-A. Statistical analysis; Biochemical Journal; vol. 173 (2), 1978, pp. 387-391.
Elleman, T.C.; et al; "Periodicity in high sulphur proteins from wool"; Nature; vol. 246, 1973, pp. 530-531.
Elod, E.: et al.; "Reactions of wool fiber and alterations in the fine structure."; Melliand Textillber; vol. 21, 1940, pp. 385-388, Abstract Only.
Elod, E.; et al.; The nature of the reactivity of wool. Melliand Textilber; vol. 21, 1940, pp. 617-622, Abstract Only.
Elod, E; et al; "The structure and reactivity of the woolen fiber. IX. The effect of H2O2 on wool."; Melliand Textilber; vol. 23, 1942, pp. 313-316, Abstract Only.
Elod,E. et al.; "The infiltration of heavy metal sulfides in the keratin fiber." Chem Ber. vol. 74B, 1941, pp. 1759-1762, Abstract Only.
Eriksson, A.; et al.; "PDGF α- and β-receptors activate unique and common signal transduction pathaways."; The EMBO Journal; vol. 11, 1992, pp. 543-550.
Filshie, B.K. et al; "The Fine Structure of α-Keratin." Journal of Molecular Biology; vol. 3, 1961, pp. 784-786.
Filshie, B.K.; Rodgers, G.E.; "An electron microscope study of the fine structure of feather keratin."; The Journal of Cell Biology; vol. 13, 1962, pp. 1-12.
Frank, S.; et al.; "Transforming growth factors β1, β2, and β3 and their receptors are differentially regulated during normal and impaired wound healing." The Journal of Biological Chemistry; vol. 271, 1996, p. 10188-10193.
Frenkel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.
Fraser, B.R.D, et al; "Intermediate Filaments in α-keratins." Proceeedings of the National Academy of Sciences, USA.; Biochemistry; vol. 83, 1986, pp. 1179-1183.
Fraser, R.D.B.; et al; "Disulphide bonding in α-keratin."; International Journal of Biological Macromolecules; vol. 10, issue 2, 1988, pp. 106-112.

Fraser, R.D.B.; et al; "Microscopic Observations of the Alkaline-Thioglycollate Extraction of Wool." Short Communications, Wool Textile Research Laboratory; vol. 12, 1953, pp. 484-485.
Fraser, R.D.B.; et al; "Molecular organization in Alpha-Keratin."; Nature; vol. 193, 1962, pp. 1052-1055.
Fraser, R.D.B.; Gillispie, J.M.; "Wool structure and biosysnthesis." Nature vol. 126 1976, pp. 650-654.
Fraser, R.D.B.; Macrae, T.P.; "Helical models of feather keratin structure." Nature; vol. 195, No. 4847, 1962, pp. 1167,1168.
Fraser, R.D.B.; MaCrae, T.P.; Rogers, G.E.; "Structure of Alpha-Keratin." Nature; vol. 183, 1959, pp. 592-594.
Fraser,R.D.B.; Gillespie, J.M.; Macrae,T.P.; "Tyrosine-rich proteins in keratins."; Comparative Biochemistry and Physiology; vol. 44B, 1973, pp. 943-949.
Fratini, A.; et al; "Dietary cysteine regulates the levels of mRNAs encoding a family of cysteine-rich proteins of wool."; Journal of Investigative Dermatology; vol. 102, 1994, pp. 178-185, Abstract Only.
Frenkel, M.J. et al.; "Heterogeneity of tyrosine-rich proteins of wool."; Proceedings of the Australian Biochemical Society; vol. 7, 1974, p. 4, Abstract Only.
Frenkel, M.J.; "Alkali susceptible amides in tyrosine-rich proteins of wool."; Proceedings of the Australian Biochemical Society; vol. 10, 1977, p. 21, Abstract Only.
Frenkel, M.J.; et al.; "Studies of the ribonucleic-acids coding for the keratin complex of hair."; Proceedings of the Australian Biochemical Society; vol. 12, 1979, p. 87, Abstract Only.
Frenkel, M.J.; et al; "Factors influencing biosynthesis of tyrosine-rich proteins of wool."; Australian Journal of Biological Sciences; vol. 27, 1974, pp. 31-38.
Frenkel, M.J.; et al.; "The keratin BIIIB gene family: isolation of cDNA clones and structure of a gene and a related pseudogene."; Genomics; vol. 4, No. 2, 1989, pp. 182-191.
Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.
Frenkel, M.J.; Gillespie, J.M.; Woods, E.F.; "The isolation and properties of a tyrosine-rich protein from wool: component 0.62.";European Journal Biochemistry; vol. 34, 1973, pp. 112-119.
Fujisawa, K.; et al; "Synthesis and characterization of zinc family thiolato complexes.";Abstracts, Symposium on Biofunctional Chemistry, vol. 14, 1999, pp. 52-53.
Fujisawa, K.; et al; "Synthesis and characterization of zinc family thiolato complexes.";Abstracts, Symposium on Biofunctional Chemistry, vol. 14, 1999, pp. 52-53. Abstract Only.
Gillespie, J.M. et al; "Evidence of homology in a high-sulphur protein fraction (SCMK-B2) of wool and hair α-keratins."; Biochemistry Journal; vol. 110, No. 2, 1968, pp. 193-198.
Gillespie, J.M. et al; "A comparative study of high-sulphur proteins from α-karatins." Comparative Biochemistry and Physiology; vol. 15, 1965, pp. 175-185.
Gillespie, J.M.; "Reaction of Sodium Borohydride with wool." Nature; vol. 183 No. 4657, 1959, pp. 322, 323.
Gillespie, J.M.; "Swelling of keratins in formic acid." Textile Research Journal; vol. 40, No. 9, 1970, pp. 853-855.
Gillespie, J.M.; "The isolation and properties of some soluble proteins from wool. (II) The preferential extracation of high-sulphur proteins."; Australian Journal of Biological Sciences; vol. 15, No. 1, 1962, pp. 262-277.
Gillespie, J.M.; "The isolation from wool of a readily extractable protein of low sulphur content." Biochimica et Biophysica Acta; vol. 27, 1958, pp. 225,226.
Gillespie, J.M.; "The probable role and location of high-glycine-tyrosine proteins in the structure of keratins." Biopolymers, vol. 17, 1978, pp. 2743-2745.
Gillespie, J.M.; "The relation between the crimp of wool and its content of high-sulfur proteins."; Textile Research Journal; vol. 35, No. 12, 1965, pp. 1128-1129.
Gillespie, J.M.; "Keratin structure and changes with copper deficiency."; *Australian Journal of Dermatology*; vol. 14, No. 3, 1973, pp. 127-131.

(56) References Cited

OTHER PUBLICATIONS

Gillespie, J.M.; Broad, A.; "A further study on the dietary-regulated biosynthesis of high-sulphur wool proteins." Biochemistry Journal; vol. 112, 1969, pp. 41-49.
Gillespie, J.M.; Darskus, R.L.; "Relation between the tyrosine content of various wools and their content of a class of protiens rich in tyrosine and glycine."; Australian Journal Biological Science; vol. 24, 1971, pp. 1189-1197.
Gillespie, J.M.; et al.; "Changes in the matrix proteins of wool and mouse hair following the administration of depilatory compounds." Australian Journal of Biological Sciences; vol. 33, 1980, pp. 125-136.
Gillespie, J.M.; et al.; "Proteins of the hard keratins of Echidna, Hedgehog, Rabbit, Ox and Man."; Australian Journal of Biological Sciences, vol. 30, 1977, pp. 401-409.
Gillespie, J.M.; et al; "The Diversity of Keratins"; Comparative Biochemistry and Physiology; vol. 47, No. 2,1974, pp. 339-346.
Gillespie, J.M.; et al; "Variable composition of hair and high-sulfur proteins in trichothiodystrophy."; Journal of Applied Cosmetology; vol. 7, No. 2, 1989, pp. 39-48.
Gillespie, J.M.; Frenkel, M.J.; "The macroheterogeneity of type I tyrosine-rich proteins of merino wool."; Australian Journal Biological Science; vol. 27, 1974, pp. 617-627.
Gillespie, J.M.; Inglis, A.S.; "High-sulphur proteins as a major cause of variation in sulphur content between α-keratins." Nature; vol. 207, 1965, pp. 1293,1294.
Gillespie, J.M.; Marshall, R.C.; "A comparision of the proteins of normal and trichothiodystrophic human hair." The Journal of Investigative Dermatology; vol. 80, 1983, pp. 195-202.
Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.
Gillespie, J.M.; Reis, P.J.; "The dietary regulated biosynthesis of high-sulphur wool proteins."; Biochemistry Journal; vol. 98, 1966, pp. 669-677.
Gillespie, J.M.; Simmonds, D.H.; "Amino acid composition of a sulphur-rich protein from wool."; Biochimica et Biophysica Acta; vol. 39, 1960, pp. 538-539.
Gillespie,J.M.; "Proteins rich in glycine and tyrosine from keratins."; Comparative Biochemistry and Physiology; vol. 41B, 1972, pp. 723-734.
Gillis, J.N.; et al.; "Selective retention of oxygen using chromatographic columns containing metal chelate polymers."; Analytical Chemistry; vol. 57(8), 1985, pp. 1572-1577.
Goddard et al., A Study on Keratin. J. Biol. Chem. 106:605-14 (1934).
Goddard, D.R. et al; "A Study on Keratin."; Journal of Biological Chemistry; vol. 106, 1934, pp. 605-614.
Gough, K.H. et al; "Amino acid sequences of alpha-helical segments from S-carboxymethylkerateine-A. Complete sequence of a type-I segment."; Biochemical Journal; vol. 173 (2), 1978, pp. 373-385.
Green, M.R.; Basketter, D.A.; Couchman, J.R.; Rees, D.A.; "Distribution and number of epidermal growth factor receptors in skin is related to epithelial cell growth.;" Developmental Biology; vol. 100, 1983, pp. 506-512.
Greven, R.; et al.; "Morphological origin of the S-carboxymethyl kerateines of wool."; Textile Research Journal vol. 56; 1986, pp. 523-526.
Grotendorst, G.R.; et al.; "Novel transforming growth factor β response element controls the expression of the connective tissue growth factor gene."; Cell Growth and Differentiation; vol. 7, 1996, pp. 469-480.
Han, C.H.; et al; "Effect of glycerol addition on the structure and properties of soluble wool keratose films."; Journal of the Korean Fiber Society; vol. 37,No. 8, 2000, pp. 442-447, Abstract Only.

Hanukoglu, I.; et al.; "The cDNA sequence of a human epidermal keratin: Divergence of the sequence but conservation of structure among intermediate filament proteins." Cell; vol. 31, 1982, pp. 243-252.
Happey, F.; "Polycrystralline structure of wool." Nature; No. 4218, 1950, pp. 397-398.
Happey, F.; Wormell, R. L.; "Regenerated keratin fibers from wool." Journal Textile Inst.; vol. 40, 1949, pp. T855-T869, Abstract Only.
Happey, F.; Wormell, R. L.; "Regenerated keratin fibers."; Nature ; vol. 163, 1949, p. 18, Abstract Only.
Harding, H.W.J.; et al; "Enzymic conversion of arginine to citrulline in a hair protein precusor."; Proceedings of the Australian Biochemical Society; ; vol. 9, 1976, p. 18, Abstract Only.
Harding, H.W.J.; Rogers, G.E.; "Formation of ε (γ-Glutamyl) lysine cross-link in hair proteins. Investigation of transamidases in hair follicles." The Journal of Biochemistry; vol. 11, No. 15, 1972 pp. 2858-2863.
Hardy, M.H.; "The Secret life of the hair follicle."; Trends in Genetics; vol. 8, No. 2, 1992, pp. 55-60.
Harrap, B.S.; et al; "Soluble derivatives of feather keratin. (I) Isolation, fractionation and amiino acid composition." Biochemistry Journal; vol. 92, 1964, pp. 8-18.
Harris, M.; et al.; "Testing for oxidation damage of wool by alkali solubility." The Textile Manufacturer; vol. 63, 1937, pp. 36,37.
Hewish, D.R.; et al; "In vitro growth and differentiation of epithelial cells derived from post-embryonic hair follicles."; Australian Journal of Biological Sciences; vol. 35, No. 1, 1982, pp. 103-109.
Hiroshi, S.; et al; "Differential Thermal Analysis of component proteins from wool." Institute for Chemical Research, Kyoto University, Uji, Kyoto; vol. 38, 1982, pp. 517-522.
Hogg, D.M.; et al; "Amino acid sequences of alpha-helical segments from S-carboxymethylkerateine-A. Tryptic and chymotryptic peptides from a type II segment."; Biochemical Journal; vol. 173(2), 1978, pp. 353-363.
Horn, J.C.; Speakman, P.T.; "Relative molecular masses of reduced wool keratin polypeptides" Biochemistry Society Transcript, vol. 14, 1986, pp. 333, 334.
Hu, J.; et al; "Preparation of stable solution of keratin from human hair and structure and properties of the cast film."; Gaofenzi Cailiao Kexue Yu Gongcheng; vol. 18 (2), 2002, pp. 131-133, Abstract Only.
Humphries, M.; "Protein-silicone copolymers."; Cosmetics News; vol. 16, No. 92, 1993, pp. 313-318, Abstract Only.
Hynd, P.I.; et al; "Amino acid transport in wool and hair follicles."; Experimental Dermatology; vol. 8, 1999, pp. 325-326, Abstract Only.
Hübner, G.; et al.; "Strong induction of activin expression after injury suggests an important role of activin in wound repair."; Developmental Biology; vol. 173, 1996, pp. 490-498.
Igarashi, A.; et al.; "Regulation of connective tissue growth factor gene expression in human skin fibroblasts and during wound repair." Molecular Biology of the Cell; vol. 4, 1993, pp. 637-645.
Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.
International Search Report and Written Opinion for PCT/US06/40673; dated Sep. 24, 2007.
Ito, H.; et al; "Biocompatability of denatured keratins from wool."; Kobunshi Ronbunshu; vol. 39(4), 1982, pp. 249-256.
Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.
Jahoda, C.A.B.; et al.; "Dermal-Epidermal Interactions: Adult Follicle-derived cell populations and hair growth."; Dermatologic Clinics; vol. 14, No. 4 1996, pp. 573-583.
Japanese Office Action Corresponding to Japanese Patent Application No. 2008-555408; dated Apr. 24, 2012; 5 pages.
Japanese Office Action corresponding to Japanese Patent Application No. 2008-536758; dated Jun. 21, 2013.
Jenkins, B.J. ; et al; "Isolation and characterization of a sheep cysteine-rich cuticle keratin pseudogene."; DNA Sequence; vol. 3, 1992, pp. 181-184, Abstract Only.

(56) References Cited

OTHER PUBLICATIONS

Jenkins, B.J. et al; "Differential expression of genes encoding a cysteine-rich keratin in the hair cuticle."; Journal of Investigative Dermatology; vol. 103, 1994, pp. 310-317, Abstract Only.
Jezowska-Trezebiatowska, B.; et al; "New cobalt (II) complexes, reversibly binding oxygen in aqueous solution."; Bulletin de l'Academie Polonaise des Sciences, Serie des Sciences Chimiques; vol. 20 (3), 1972, pp. 187-192, Abstract Only.
Johnson, P.C.; et al; "Oxidative metabolism and blood flow regulation: The search for the missing link."; Journal of Vascular Research; vol. 37 (1) 2000, p. 83, Abstract Only.
Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.
Jones, L.N.; "Studies on Microfibrils from alpha-Keratin."; Biochimica et Biophysica Acta ; vol. 446. 1976, pp. 515-524.
Jones, L.N.; et al; "Studies of developing human hair shaft cells in vitro."; Journal of Investigative Dermatology; vol. 90, No. 1, 1988, pp. 58-64.
Jozefowicz, M.; Jozefonvicz, J; "Functional Polymers and Cells"; Biomaterials; vol. 16, No. 4, 1988, pp. 831-870.
Katoh, K.; et al; "Multi-functionalization of fiber made of natural polymer."; Aichi-ken Sangayo Gijutsu Kenkyusho Kenkyu Hokoku; vol. 1, 2002, pp. 174-177, Abstract Only.
Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.
Kawano, Y.; et al; "Film and gel of keratins."; Kagaku to Seibutsu; vol. 13 (5), 1975, pp. 291-292, Abstract Only.
Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.
Kemp, D.J.; Rodgers, G.E.; "Immunological and immunofluorescent studies on keratin of the hair follicle."; Journal of Cell Science; vol. 7, 1970, pp. 273-283.
Kikkawa, M.; et al; "Solubilization of keratin. Solubilization of feather keratin by oxidation with performic acid."; Hikaku Kagaku,(Leather Chemistry) vol. 20(3), 1974, pp. 151-162, Abstract Only.
Klement, V.; et al; "The use of computer-analysis for the quantification of 2-D electrophoretic hair keratin patterns—a pilot study."; Journal of the Forensic Science Society; vol. 24, No. 4, 1984, p. 440, Abstract Only.
Koga, J. et al.; "FTIR study on structural transformation of keratin films induced by stretching."; Journal of Applied polymer Science; vol. 37, 1989, pp. 2131-2140.
Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.
Kowalska, K.; et al; "New bacterial peptides isolated from structural proteins (keratin of porcine bristle)."; Peptides; Proceedings of the European Peptide Symposium, 25th, 1998, pp. 792-793, Abstract Only.
Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.
Kuczek, E.S.; et al; "Sheep wool (glycine+tyrosine)-rich keratin genes: a family of low sequence homology."; European Journal of Biochemistry; vol. 166, 1987, pp. 79-85.
Kulkarni, V.G.; "Further studies on the microfibrils from wool keratin. Part I: the isolation of microfibrils."; Textile Research Journal; vol. 46, No. 11, 1976, pp. 833-835.
Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, p. 818, Abstract Only.

Kvedar, J.C.; et al.; "Cytokeratins of the bovine hoof: classification and studies on expression."; Biochimica et Biophysica Acta; vol. 884, 1986, pp. 462-473.
Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.
Laplaza, C.E.; et al; "Helix-loop-helix-peptide as scaffolds for the construction of bridged metal assemblies in proteins: The spectroscopic A-cluster structure in carbon monoxide dehydrogenase."; Journal of the American Chemical Society, vol. 123, (42), 2001, p. 10255-10264.
Lee SJ et al. Tissue Engineering Scaffolds From Self-assembled Human Hair Keratins (2005) Polymer Preprints 46(1):112.
Lee, K.Y.; "Characterization of Silk Fibroin/S-carboxymethyl kerateine surfaces: Evaluation of the biocompatibility by contact angle measurement."; Fibers and Polymers; vol. 2, No. 2, 2001, pp. 71-74.
Leeder, J.D.; et al; "Readily extracted proteins from Merino wool."; Textile Research Journal; vol. 52, No. 4, 1982, pp. 245-249.
Lennox, F.G.; "Protein fibers. Chemistry."; Review of Textile Progress Journal; vol. 17, 1967, pp. 81-97, Abstract Only.
Lennox, F.G.; et al.; "Photochemical degradation of keratins."; Photochemistry and Photobiology; vol. 9, No. 4, 1969, pp. 359-367.
Leon, N.H.; "The chemical reactivity and modification of keratin fibres." Textile Progress vol. 7, No. 1975, pp. 1-81.
Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.
Ley, K.; et al; "Release of cuticle from wool by agitation in solutions of detergents."; Australian Journal of Biological Sciences; vol. 41, No. 2, 1988, pp. 163-176, Abstract Only.
Ley, K.F.; et al; "Wool cuticle—new approaches to its production and protein characterization."; Proceedings of the Australian Biochemical Society; vol. 14, 1981, p. 14, Abstract Only.
Li, C-X.; et al al; "Purification of natural antikeratin autoantibodies from natural human serum and their effect on human keratinocytes cultured in vivo."; British Journal of Dermatology; vol. 145, No. 5, 2001, pp. 737-748.
Lindley, H. et al.; "High-sulfur protein fractions of keratins."; *Applied Polymers Symposium*; vol. 18, No. 1, 1971, pp. 21-35.
Lindley, H.; et al; "The occurance of the Cys-Cys sequence in keratins."; Journal of Molecular Biology; vol. 30, No. 1, 1967, pp. 63-67.
Lindley, H.; et al; "The preparation and properties of a group of proteins from the high sulphur fraction of wool"; Biochemical Journal; vol. 128, No. 4, 1972, pp. 859-867.
Lindley, H.; et al; "The reactivity of the disulphide bonds of wool"; Biochemical Journal; vol. 139, No. 3, 1974, pp. 515-523.
Lindley,, H.; et al; "Disulphide interchange reactions involving cyclosystine and their relevance to problems of α-keratin structure" Biochemical Journal; vol. 108, No. 4, 1968, pp. 701-703.
Lissizin, Th.; "Behavior of keratin sulfur and cystin sulfur, in the oxidation of these proteins by potassium permanganate." Biochemistry Bulletin vol. 4, 1915, pp. 18-23, Abstract Only.
Lissizin, Th.; "The oxidation products of keratin by oxidation with permanganate." Z. Physiology Chem. vol. 173, 1928, pp. 309-311, Abstract Only.
Liu, S.M.; et al.; "Transsulfuration, protein synthesis rate and follicle mRNA in the skin of young Merino lambs in response to infusions of methionine and serine."; British Journal of Nutrition; vol. 83, No. 4, 2000, pp. 401-409.
Lotay, S.S.; Speakman, P.T.; "Three-chain merokeratin from wool may be a fragment of the microfibril component macromolecule"; Nature; vol. 265, 1977, pp. 274-277.
Lyons, K.M.; et al.; "Patterns of expression of murine Vgr-1 and BMP-2a RNA suggest that transforming growth factor-β-like genes coordinately regulate aspects of embryonic development." Genes & Development; vol. 3, 1989, pp. 1657-1668.
Mack, J.W.; Torchia, D.A.; Steinert, P.M.; "Solid-State NMR Studies of the Dynamics and Stucture of Mouse Keratin Intermediate Filaments."; Biochemistry; vol. 27, No. 15. 1988, pp. 5418-5426.

(56) References Cited

OTHER PUBLICATIONS

MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.
MacLaren, J.A.; "The extent of reduction of wool proteins by thiols." The Australian Journal of Chemistry; vol. 15,No. 4, 1962, pp. 824-831.
Marikovsky, M.; et al.; "Appearance of heparin-binding EGF-like growth factor in wound fluid as a response to injury."; Proceedings of the National Academy of Sciences, USA; vol. 90, 1993, pp. 3889-3893.
Marshall, R.C. et al; "High-sulfur proteins in mammalian keratins: a possible aid in classification."; Australian Journal of Zoology; vol. 25, No. 1, 1977, pp. 121-132, Abstract Only.
Marshall, R.C.; "Successful isoelectric-focusing of wool low-sulphur proteins.";Journal of Chromatography; vol. 172, 1979, pp. 351-356.
Marshall, R.C.; "Analysis of the proteins from single wool fibers by two-dimensional polyacrylamide-gel electrophoresis."; Textile Research Journal; vol. 51, No. 2, 1981, pp. 106-108.
Marshall, R.C.; "Changes in wool low-sulphur and high-sulphur protein-components following chemical defleecing."; Textile Research Journal; vol. 51, No. 6, 1981, p. 384-388.
Marshall, R.C.; "Characterization of the proteins of human hair and nail by electrophoresis."; Journal of Investigative Dermatology; vol. 80, No. 6, 1983, pp. 519-524.
Marshall, R.C.; "Cysteine-rich proteins of mouse hair."; Proceedings of the Australian Biochemical Society; vol. 8, 1975, p. 4, Abstract Only.
Marshall, R.C.; "Forensic identification of hairs by electrophoresis."; Journal of the Forensic Society; vol. 24, No. 4, 1984, p. 340. Citation Only.
Marshall, R.C.; "Genetic variation in the proteins of human nail."; Journal of Investigative Dermatology; vol. 75, No. 3, 1980, pp. 264-269.
Marshall, R.C.; et al; "An investigation of the relationship of wool textile properties to fiber protein composition."; Proceedings of the International Wool Textile Research Conf.; vol. 1, 1990, pp. 266-275, Abstract Only.
Marshall, R.C.; et al; "Examination of proteins of wool cuticle by two-dimensional gel-electrophoresis."; Textile Research Journal; vol. 56, No. 12, 1986, pp. 772-774.
Marshall, R.C.; et al; "High sulfur proteins and α-keratins II.* Isolatioin and partial characterization of purified components from mouse hair."; Australian Journal of Biological Sciences.; vol. 29, 1976, pp. 11-20.
Marshall, R.C.; et al; "High sulphur proteins from α-keratins I. Heterogeneity of the proteins from mouse hair."; Australian Journal of Biological Sciences; vol. 29, 1976, pp. 1-10.
Marshall, R.C.; et al; "Possible identification of specialty fibers y electrophoresis."; Textile Research Journal; vol. 54, No. 2, 1984, pp. 126-128.
Marshall, R.C.; et al; "Protein changes after short thermal treatments of wool fibrics."; Textile Research Journal; vol. 53, No. 12, 1983, pp. 792-794.
Marshall, R.C.; et al; "Sequence studies of wool proteins rich in glycine and aromatic residues."; Proceedings of the Australian Biochemical Society; vol. 12, 1979, p. 12.
Marshall, R.C.; Gillespie, J.M.; "The keratin proteins of wool, horn and hoof from sheep." Australian Journal of Biological Sciences; vol. 30, 1977, pp. 389-400.
Marshall, R.C; et al.; "Heterogeneity and incomplete disulfide reduction in the high sulphur proteins of wool." Australian Journal of Biological Sciences; vol. 31, 1978, pp. 219-229.
Martin, P. "Wound Healing-Aiming for Perfect Skin Regeneration."; Science; vol. 276, 1997, pp. 75-81.
Mason, E.D.; et al.; "Dorsal midline fate in *Drosophila* embryos requires twisted gastrulation, a gene encoding a secreted protein related to human connective tissue growth factor." Genes and Development vol. 8, 1994, pp. 1489-1501.

Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29, Abstract Only.
Mazzoni, M.C.; et al; "Blood and plasma viscocity and microvascular function in hemodilution. A perspective from LaJolla, California."; European Surgical Research; vol. 34, (1-2), 2002 Ref. 35, Abstract Only.
McCloghry, C.E.; et al; "Wool follicles initiate, develop and produce fibres in ovine foetal skin grafts."; Proceedings of the Australian Society of Animal Production; vol. 18, 1990, p. 518, Abstract Only.
McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.
McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.
Mies, H.H.; et al.; "Preparation of soluble proteins from wool."; Leder; vol. 39, 1988, pp. 1-9, Abstract Only.
Mies, H.H.; Zahn, H.; "Chromatographic and electrophoretic investigations of the properties of unprotected low-sulphur wool keratins."; Journal of Chromatography; vol. 405, 1987, pp. 365-370.
Migneault I et al. Glutaraldehyde: behavior in aqueous solution, reaction with proteins, and application to enzyme crossing. BioTechniques. 2004; 37(5): 790-802.
Mitsui S, Ohuchi A, Hotta M, Tsuboi R, Ogawa H. Genes for a range or growth factors and cyclin-dependent kinase inhibitors are expressed by isolated human hair follicles. *British J Dermatol*. 1997; 137: 693-698.
Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.
Miwa, M.; et al; "Effects of fiber length on the tensile strength of epoxy/glass fiber and polyester/glass fiber composites." Journal of Applied Polymer Science; vol. 25, 1980, pp. 795-807.
Miyamoto, T.: et al; "Sorption Behavior of Heavy Metal Ions on S-Subtituted Kerateine Gels." Institute for Chemical Research; vol. 34, No. 10, 1978, pp. T-447-T-454.
Moll, R.; et al.; "The catalog of humans cytokeratins: Patterns of expression in normal epithelia, tumors and cultured cells." Cell; vol. 31, 1982, pp. 11-24.
Mueller, R.V.; et al.; "The effect of insulinlike growth factor I on wound healing variables and macrophages in rats." Archives of Surgery; vol. 129, 1994, pp. 262-265.
Nakamura, A.; et al; "Cysteine-containing oligopepetide model complexes of iron-sulfur proteins."; Advances in Inorganic Chemistry; vol. 33, 1989, pp. 39-67, Abstract Only.
Nakamura, Y.; et al; "Cystine in wool. Relation between sulfhydryl group and supercontraction." Sen-i Gakkaishi, vol. 16, 1960, pp. 852-858, Abstract Only.
Nancarrow, M.J. et al; "Expression of ornithine decarboxylase during embryonic development of wool follicles."; Experimental Dermatology; vol. 8, 1999, pp. 326-328.
NeuColl, Inc., Clinical Performance of Collagraft® Bone Graft Matrix in the Management of Fractures and Osseous Defects in the Appendicular Skeleton (Jan. 2000).
Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227, Abstract Only.
Norman, J.A.T.; et al; "Reversible complexes for the recovery of dioxygen."; Procedings of the Annual IUCCP Symposium; 1987, pp. 107-125, Abstract Only.
O'Donnell IJ et al. Studies on Oxidized Wool IV. Fractionation of Proteins Extracted from Wool on DEAE-cellulose Using Buffers Containing 8M Urea (1961) Aust J Biol Sci 14:461-474.
Okamoto, S.; "Formation of films from some proteins."; Nippon Shokuhin Kogyo Gakkaishi; vol. 24(1), 1977, pp. 40-50, Abstract Only.

(56) References Cited

OTHER PUBLICATIONS

O'Shea, J.M.; et al; "The effect of ultrasonic irradiation on proteins." Australian Journal of Biological Sciences; vol. 26,1973, pp. 583-590.
Osterberg, R.; "Metal complexes of peptides."; Metal Catalog Lipid Oxidation; Sv. Inst. Konserveringsforsk, Symposium, Goteberg Sweden, 1967, pp. 119-127, Abstract Only.
Panteleyev, A.A.; et al.; "Hair follicle predetermination."; Journal of Cell Science; vol. 114, 2001, pp. 3419-3431.
Parry, D.A.D.; et al; "Fibrous proteins: Scientific, Industrial and Medical aspects."; An Academic Press Fast Publication; vol. 1, 1979, pp. 1-132.
Parry, D.A.D.; et al; "Structure of α-keratin: Structural implication of the amino acid sequences of the type I and type II chain segments."; Journal of Molecular Biology; vol. 113, 1977, pp. 449-454.
Pauling, L.; Corey, R.B.; "The structure of feather rachis keratin." Proceedings of the National Academy of Sciences; vol. 37, No. 5, 1951, pp. 256-261.
Pauling, L.; Corey, R.B.; "The structure of hair, muscle, and related proteins."; Proceedings of the National Academy of Sciences; vol. 37, No. 5, 1951, pp. 261-271.
Peters, L.; "Affinity of ions for keratin."; Journal of Textile Institute; vol. 58, No. 4, 1967, pp. 179-180.
Peus, D., et al.; "Growth factors in hair organ development and the hair growth cycle." Dermatologic Clinins; vol. 14, No. 4, 1996, pp. 559-572.
Philpott, M.P.; et al.; "Whole hair follicle culture." Dermatologic Clinics; vol. 14, No. 4, 1996, pp. 595-607.
Powell, B.C.; "The keratin proteins and genes of wool and hair."; Wool Technology and Sheep Breeding; vol. 44, No. 2, 1996, pp. 100-118, Abstract Only.
Powell, B.C.; et al; "The Notch signalling pathway in hair growth."; Mechanisms of Development; vol. 78, 1988, pp. 189-192. Abstract Only.
Powell, B.C.; et al; "Characterization of a gene encoding a cysteine-rich keratin associated protein synthesized late in rabbit hair follicle differentiation."; Differentiation; vol. 58, 1995, pp. 227-232.
Powell, B.C.; et al; "Characterization of hair (wool) keratin intermediate filament gene domain."; Journal of Investigative Dermatology; vol. 102, 1994, pp. 171-177, Abstract Only.
Powell, B.C.; et al; "Mammalian keratin gene families: organization of genes coding for the B2 high sulphur proteins of sheep wool."; Nucleic Acids Research; vol. 11, 1983, pp. 5327-5346.
Powell, B.C.; et al; "Regulation of Keratin Gene Expression in Hair Follicle Differentiation." Annals New York Academy of Sciences; vol. 642, 1991, pp. 1-20.
Powell, B.C.; et al; "The role of keratin proteins and their genes in the growth, structure and properties of hair."; EXS; vol. 78, 1997, pp. 59-148 Ref: 284, Abstract Only.
Powell, B.C.; et al; "Transgenic sheep and wool growth: possibilities and current status."; Reproduction, Fertility, and Development; vol. 6, 1994, pp. 615-623, Abstract Only.
Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.
Powell, B.C.; Rodgers, G.E.; "Cyclic hair-loss and regrowth in the transgenic mice overexpressing and intermediate filament gene."; The EMBO Journal vol. 9, No. 5, 1990, pp. 1485-1493.
Rana, T.M.; et al; "Specific cleavage of a protein by an attached iron chelate."; Journal of the American Chemical Society; vol. 112 (6), 1990, pp. 2457-2458.
Randall, V.A.; "The use of dermal papilla cells in studies of normal and abnormal hair follicle biology."; Dermatologic Clinics; vol. 14, No. 4 1996 pp. 585-594.
Ranford, J.D.; et al; "Matallodrugs. The role of thiolate proteins and metal-thiolate complexes."; Metallothioneins, Conference General Review; 1992, pp. 408-435, Abstract Only.
Ranshoff, S.; et al; "Synthesis and characterization of new dioxygen carriers: a reexamination of the fly-over ligand system."; Inorganic Chemistry; vol. 29(16), 1990, pp. 2945-2947.
Raphael, K.A.; et al; "Protein and amino acid composition of hair from mice carrying the naked (N) gene."; Genetic Research, vol. 44, No. 1, 1984, pp. 29-38.
Rappolee, D.A.; et al.; "Wound macrophages express TGF-α and other growth factors in vivo: Analysis by mRNA phenotyping."; Science; vol. 241, 1988, pp. 708-712.
Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.
Reis, P.J.; "Influence of dietary protein and methionine on the sulphur content and growth rate of wool in the millk fed lambs" Australian Journal of Biological Science; vol. 23, No. 1, 1970, pp. 193-200.
Reis, P.J.; "The growth and composition of wool—III. Variations in the sulphur content of wool."; Australian Journal of Biological Sciences; vol. 18, 1965, pp. 671-687.
Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.
Reis, P.J.; et al; "The utilization of abomasal supplements of proteins and amino acids by sheep with special reference to wool growth"; Australian Journal of Biological Sciences; vol. 25, 1972, pp. 1057-1071.
Reis, P.J.; et al; "The influence of abomasal and intervenous supplements of sulphur containing amino acids on wool growth rate"; Australian Journal of Biological Sciences; vol. 26, No. 1, 1973, pp. 249-258.
Reis, P.J.; et al; "The nutritional control of the growth and properties of mohair and wool fibers: a comparative review"; Journal of Animal Science; vol. 72, No. 7, 1994, pp. 1899-1907.
Reis, P.J.; Gillespie, J.M.; "Effects of phenylalanine and the analogues of methionine and phenylalanine on the composition of wool and mouse hair." Australian Journal of Biological Sciences; vol. 38, No. 2 pp. 151-163.
Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.
Reis, P.J.; "Variations in the S content of wool."; Biology Skin Hair Growth, Proceedings Symposium; 1964, pp. 365-375, Abstract Only.
Rogers, G.E.; et al; "Keratin protofilaments and ribosomes from hair follicles."; Nature, vol. 205, 1965, pp. 77-78.
Rogers, G.E et al.; "An approach to the investigation of protein biosynthesis in hair follicles." *Biology of Skin Hair Growth, Proceedings*, 1965, pp. 329-343.
Rogers, G.E.; "Some observations on the proteins of the inner root sheath cells of hair follicles." Biochimica et Biophysica Acta; vol. 29. 1958, pp. 33-43.
Rogers, G.E.; "Genetic engineering for novel fibres."; Journal of the Textile Institute; vol. 91, part 3, Special Issue, 2000, pp. 24-31.
Rogers, G.E.; "Improvement of wool production through genetic engineering."; Trends in biotechnology(Personnal edition); vol. 8, 1990, pp. 6-11, 32 references, Abstract Only.
Rogers, G.E.; "Proteins of the inner-root-sheath cells of hair follicles."; Biochimica et Biophysica Acta; vol. 29, 1958, pp. 33-43, Abstract Only.
Rogers, G.E.; "Structural and biochemical features of the hair follicles."; Epidermis; 1964, pp. 179-236. Citation Only.
Rogers, G.E.; "Structure and biochemistry of keratin."; The Biological Basis of Medicine.; vol. 6, 1969, pp. 21-57, Abstract Only.
Rogers, G.E.; "Synthesis and cross-linking in the structure and growth of hair keratins." Clinics in Dermatology; vol. 6, No. 4, 1988, pp. 26-31. Abstract Only.
Rogers, G.E.; et al; "Protein biosynthesis in hair follicles."; Biology of Skin Hair Growth., Proceedings ; 1965, pp. 329-343, Abstract Only.

(56) References Cited

OTHER PUBLICATIONS

Rogers, G.E.; et al; "A procedure for the culture of hair follicles as functionally intact organoids."; Clinics in Dermatology; vol. 6, No. 4, 1988. pp. 36-41, Abstract Only.
Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184. Abstract Only.
Rogers, G.E.; et al; "Themes in the molecular structure of hair—discussion." Annals New York Academy Science; vol. 642, 1991, pp. 100-106.
Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.
Ross, S.A.; et al; "Nickel complexes of cysteine- and cystine-containing peptides: Spontaneous formation of disulfide-bridged dimers at neutral pH."; Inorganic Chemistry, vol. 37 (20), 1998, pp. 5358-5363.
Rouse, J.G.; et al; "A review of keratin-based biomaterials for biomedical applications." Materials; vol. 3, 2010, pp. 999-1014.
Rowlands, R.J.; "Periodicity in high-sulphur proteins from wool."; Nature; vol. 246, No. 5434, 1973, pp. 530-531.
Sadova, S. F.; et al; "Grafting of vinyl monomers onto wool keratin in an oxidation-reduction system."; Zh. Vses. Khim. O-va, vol. 12(5), 1967, pp. 596-597, Abstract Only.
Sander, G.; et al; "Expresssion of the homeobox gene, Barx2, in wool follicle development."; Journal of Investigative Dermatology; vol. 115, No. 4, 2000, pp. 753-756.
Sauk, J.J. et al; "Reconstitution of cytokeratin filaments in vitro: Further evidence for the role of nonhelical peptides in filament assembly."; The Journal of Cell Biology; vol. 99, 1984, pp. 1590-1597.
Schaller, J.; et al; "Membranes prepared from keratin-polyacrylonitrile graft copolymers." Journal of Applied Polymer Sciences; vol. 25(5), 1980, pp. 783-794.
Schornig, M.; Heumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, pp. 1471-1479.
Schrooyen, P.M.M.; et al; "Biodegrable films from selectively modified feather keratin dispersions."; Polymer Preprints; vol. 39, No. 2, 1998, p. 160, Abstract Only.
Schrooyen, P.M.M.; et al; "Polymer films from chicken feather keratin."; Book of Abstracts, American Chemical Society National Meeting Boston, 1998, Abstract Only.
Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.
Sizin, T.L.; "The occurance of azelaic acid among the oxidation products of keratin." Z. Physiology Chemistry: vol. 62, 1910, pp. 226-228, Abstract Only.
Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.
Smith, A.L.; et al; "Oxidation of Wool—The Effect of Hydrogen Peroxide." Rayon Textile Monthly; vol. 39, 1936. pp. 39,40.
Smith, A.L.; et al; "Oxidation of Wool: The lead acetate test for hydrogen peroxide bleached wool." Journal of Research of the National Bureau of Standards, vol. 16, 1936, pp. 309-312.
Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.
Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.
Stary, Z.; "Brominated keratin and oxykeratin."; Z. Physiology Chemistry; vol. 144, 1925, pp. 147-177, Abstract Only.
Stary, Z.; "Solubility and digestibility of the degradation products of albumoids." Z. Physiology Chemistry; vol. 136, 1924, pp. 160-172, Abstract Only.
Steinert, P.M.; et al; "In vitro studies on the synthesis of guinea pig hair keratin proteins." Biochimica et Biophysica Acta; vol. 312, 1973, pp. 403-412.
Stenn, K.S.; "The molecular and structural biology of hair, Introduction."; Annals of New York Academy of Sciences; vol. 83, 1959, pp. 359-512.
Stenn, K.S.; et al.; "Controls of hair Follicle cycling . . . "; Physiological Reviews; vol. 81, No. 1, 2001, pp. 449-494.
Stenn, K.S.; et al.; "Hair follicle growth controls." Dermatologic Clinics; vol. 14, No. 4, 1996, pp. 543-558.
Stenn, K.S.; et al.; "Molecules of the cycling hair follicle—a tabulated review." Journal of Dermatalogical Science 7(Suppl.) 1994, pp. 109-124.
Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.
Stokes, G.D.; Dunson, W.A.; "Passage of water and electrolytes through natural and artificial keratin membranes." Desalination; vol. 42, 1982, pp. 321-328.
Struessmann, A.; et al.; "Specific radiolabeling of keratin proteins by amidination."; Journal of Chromatography, vol. 268, 1983, pp. 306-310.
Supplementary European Search Report and Opinion, EP 07750473, dated Feb. 2, 2010.
Supplementary European Search Report and Search Opinion, EP 06836364, dated Feb. 3, 2011.
Suzuki, E.; et al; "X-ray diffraction and infrared studies of an $\alpha$-helical fragment from $\alpha$-keratin." Journal of Molecular Biology; vol. 73, 1973, pp. 275-278.
Tachibana A et al. Rapid fabrication of keratin-hydroxyapatite hybrid sponges toward osteoblast cultivation and differentiation. *Biomaterials*. 2005; 26: 297-302.
Tachibana, A. et al.; "Fabrication of wool keratin sponge scaffolds for long-term cell cultivation." Journal of Biotechnology, vol. 93, 2002 pp. 165-170.
Tanabe, T.; Tachibana, A.; Yamauchi, K.; "Keratins: prospective proteinous biomaterial."; Recent Research Developments in Protein Engineering; vol. 1(Pt.2),2001, pp. 247-259.
Tazawa, T.; et al; "Anti-hair keratin monoclonal antibody (HKN-2)."; The Journal of Dermatology; vol. 12, 1985, pp. 313-317.
Thomas H et al. In vitro reconstitution of wool intermediate filaments. Int. *J. Biol. Macromol.* Oct. 1986; 8: 258-264.
Thomas, H.; et al; "Isolation of the microfibrillar proteins of wool in the disulfide form." Melliand Textilberichte; vol. 65, No. 3, 1984, pp. 208-209, Abstract Only.
Thompson et al., Studies on Reduced Wool. *Aust. J. Biol. Sci.* 15:757-68 (1962).
Tsai, A.G.; et al; "High viscocity plasma expanders: Volume restitution fluids for lowering the transfusion trigger."; Biorheology, vol. 38 (2-3), 2001, pp. 229-237, Abstract Only.
Tsai, A.G.; et al; "The unusual properties of effective blood substitutes."; Keio Journal of Medicine; vol. 51 (1), 2002, pp. 17-20, Abstract Only.
Tsuchida, E.; "Oxygen ligation of macromolecule-porphyrin complexes."; Journal of the Chemical Society of Japan; No. 6, 1988, pp. 845-852. Abstract Only.
Tsuchida, E.; et al; "Cobalt (II)/poly(ethyleneimine) membrane with oxygen binding ability."; Makromolekulare Chemie; vol. 3 (10), 1982, pp. 693-696, Abstract Only.
Tucker, D.J.; et al; "Variations in goat fiber proteins."; Australian Journal of Agriculture Research vol. 40, No. 3, 1989, pp. 675-683, Abstract Only.
Ueyama, N.; et al; "A novel method for determining the chelation ability of the cysteine-containing peptides with 3,4-toluenedithiol.

(56) References Cited

OTHER PUBLICATIONS

Application to .cents .2Fe—2S-ferredoxin model systems."; Bulletin of the Chemical Society of Japan; vol. 60 (1), 1987, pp. 283-287, Abstract Only.
Van Dyke, JP 2008-536758, Office Action dated Jul. 10, 2012.
Van Neste, D.; "The growth of human hair in nude mice."; Dermatologic Clinics; vol. 14, No. 4, 1996, pp. 609-617.
Vasak, M.; et al; "Metal thiolate clusters in cobalt (II)-metallothionein."; Proceedings of the National Academy of Sciences of the United States of America; vol. 78 (11), 1981, pp. 6709-6713.
Vogeli, G.; et al; "High-Sulfur Protein Gene Expression in a Transgenic Mouse." Annals New York Academy of Sciences; vol. 642, 1991, pp. 21-30.
Ward, K.A.; "Changes in wool follicle keratinocyte protein-biosynthesis mediated by inhibitors of follicle bulb cell-proliferation."; Proceedings of the Australian Biochemical Society; vol. 9, 1976, vol. 9, p. 57. Citation Only.
Ward, K.A.; "Study of keratin biosynthesis in isolated wool follicle cells." Proceedings of the Australian Biochemical Society; vol. 7, 1974, p. 93, Abstract Only.
Ward, K.A.; et al.; "The structure of the wool keratin microfibrillar genes." Proceedings of the Australian Biochemical Society; vol. 15, 1983, p. 70, Abstract Only.
Weber, K.; Geisler, N.; "The structural relation between intermediate filament proteins in living cells and the alpha-keratins of sheep wool" The EMBO Jjournal; vol. 1 No. 10, 1982, pp. 1155-1160.
Weiss, R.A.; Guilett, Y.A.G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.
Werner, S.; et al.; "Large induction of keratinocyte growth factor expression in the dermis during wound healing." Proceedings of the National Academy of Sciences, USA; vol. 89, 1992, pp. 6896-6900.
Whitbread, L.A.; et al; "Expression of the intermediate filament gene, K15, in the basal cell layers of epithelia and the hair follicle."; Experimental Cell Research; vol. 244, 1998, pp. 448-459, Abstract Only.
Widra, A.; "Ascoporogenesis by nannizzia grubyia on a soluble fraction of keratin." Mycopathologia et Mycologia Applicata; vol. 30, No. 2, 1966 pp. 141-144.
Wilson, B. W.; et al.; "Complete sequence of a type-I microfibrillar wool keratin gene."; Gene; vol. 73, No. 1, 1988, pp. 21-31, Abstract Only.
Wilson, N.; et al.; "The role of BMP-2 and BMP-4 in follicle initiation and the murine hair cycle."; Experimental Dermatology; vol. 8, No. 4, 1999, pp. 367-368.
Wolski, T.; Szumilo, H.; "Studies on the kinetics of dissolving feather keratin in the water-urea system." Acta Alimentaria Polinica; vol. 8, (32) No. 1-2, 1982, pp. 102-108.
Wormell, R. L.; "Regenerated fibers from wool." Brit. Rayon Silk Journal; vol. 26, No. 309, pp. 55, 1950.
Wormell, R.L.; "Regenerated protein fibres from wool and casein"; The Journal of the Textile Institute; vol. 39, 1948, T219-T224.
Wormell, R.L.; "Wool, silk and regenerated protein fibers-chemistry." Rev. Textile Progress; vol. 9, 1957, pp. 51-62, Abstract Only.
Wortmann, F.J.; et al.; "A method for isolating the cortex of keratin fibers."; Textile Research Journal; vol. 52, 1982, pp. 479-481.
Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.

Yamamura, T.; et al; "Conformation control of peptides by metal ions. Coordination confirmation correlation observed in a model for Cys-X-Y-Cys/M2+ in proteins."; Inorganic Chemistry; vol. 36 (21), 1997, pp. 4849-4859.
Yamauchi, K. et al.; "Novel proteinous microcapsules from wool keratins." Colloids and Sudaces, B: Biointerfaces; vol. 9, 1997, pp. 117-119, Abstract Only.
Yamauchi, K.; "Dissolution of hair and wool. Keratin polymers." Kobunshi Kako; vol. 4i, No. 1, 1994, pp. 14-19, Abstract Only.
Yamauchi, K.; "Perspective in chemistry and applications of keratins." Kobunshi; vol. 50, No. 4, 2001, pp. 240-243, Abstract Only.
Yamauchi, K.; "Polymer films fom keratin."; Fragrance Journal; vol. 21 (5), 1993, pp. 62-67, Abstract Only.
Yamauchi, K.; "Preparation of stable aqueous solution of keratins, and physicochemical and biochemical properties of films." Polymer Preprints—American Chemical Society, Division of Polymer Chemistry; vol. 39, No. 1, 1998, pp. 357-358, Abstract Only.
Yamauchi, K.; et al.; "Cultivation of Mouse L929 Fibroblast Cells on Keratins."; Kobunshi Gakkai Yokoshu (Polymer Preprints), Japan; vol. 44, No. 3, 1995, p. 503. Citation Only.
Yamauchi, K.; et al.; "Preparation of stable aqueous solution of keratins, and physicochemical and biodegradational properties of films." Journal of Biomedical Materials Research; vol. 31, No. 4, 1996, pp. 439-444, Abstract Only.
Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472, Abstract Only.
Yamauchi, The development of Keratin: Characteristics of Polymer Films. Fragrance J. 21(5):62-67 (1993). (English Translation of Entire Document).
Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.
Yoshimizu, H.; et al; "C CP/MAS NMR study of the conformation of stretched or heated low-sulfur keratin protein films." Macromolecules,; vol. 24, 1991, pp. 862-866.
Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230.
Zahn, H. et al.; "Reactivity of amino acid side chains. 18. Reactions of p-fluoro-m,m'-dinitrodiphenyl sulfone and p,p'-difluro-m,m'-dinotrodiphenyl sulfone with wool keratin and silk fibroin."; Kolloid Zeitschrift fuer Polymere; vol. 5, 1973 pp. 289-298, Abstract Only.
Zahn, H. et al.; "Wool as a biological composite structure."; Industrial & Engineering Chemistry Product Research and Development; vol. 19, 1980, pp. 496-501.
Zahn, H.; "Progress reporton hair keratin research."; International Journal of Cosmetic Science; vol. 24, 2002, pp. 163-169.
Zahn, H.; "Structure and chemistry of wool fibers." Kolloid-Z; vol. 100, 1942, pp. 283-298. Abstract Only.
Zahn, H.; "The role of mohair keratin research." Melliand Textilberichte; vol. 72, 1991, pp. 926-931, Abstract Only.
Zahn, H.; "Wool research taking part in comtemporary chemistry and physics." Arbeitsgemeinschaft Forsch. Landes Nordheim-Westfalen; vol. 75, 1957, pp. 47-80, Abstract Only.
Zahn, H.G.; et al; "2-Dimensional keratin patterns of human hair including cosmetically treated ones."; Journal of Forensic Science Society; vol. 24, No. 4, 1984, p. 432. Citation Only.
Zahn,H. et al.; "Wool as a biological compounding material." Schriftenreihe des Deautschen Wollforschungsintitutes; vol. 76, 1978, pp. 18-25, Abstract Only.

* cited by examiner

Viscosity curves for α-keratose (bottom curve) and α-SCMK (top curve).

Figure 3. SEM micrographs of keratose formulations (as defined in Table 1).

Figure 4. Kill curves for an antibiotic containing keratin biomaterial.

Figure 5. Release kinetics for KBAP formulations containing Cefazolin.

Figure 6. Growth of bovine osteoblasts in the presence of six different KBAP formulations compared to control conditions (media alone).

KERATIN BIOCERAMIC COMPOSITIONS

RELATED APPLICATIONS

This application claims the benefit of U.S. Provisional Patent Application Ser. No. 60/728,971, filed Oct. 21, 2005, the disclosure of which is incorporated by reference herein in its entirety.

FIELD OF THE INVENTION

The present invention concerns bioceramic bone graft compositions and methods of using the same.

BACKGROUND OF THE INVENTION

Bone loss following bone fracture is a significant problem. Indeed, bone loss in combination with infection can lead to chronic osteomyelitis and non-union. Since the first report of incorporating antibiotics into bone cement in 1970, many hospitals have adopted the practice for prophylactic treatment during arthroplasty, as well as for arrest of chronic infections (McQueen M et al., *Int Ortho* 1987; 11:241-3; Fish D N et al., *Am J Hosp Pharm* 1992; 49: 2469-74; Hanssen A D and Osmon D R. *Clin Ortho Rel Res* 1999; 369(1): 124-38; Hanssen A D. J Arthroplas 2002; 17(4S1): 98-101).

The use of antibiotic-impregnated poly(methylmethacrylate) (PMMA) beads has also become widespread (Henry S L et al., *Ortho Rev* 1991; 20(3): 242-7; Popham G J et al., *Ortho Rev* 1991; 20(4): 331-7; Klemm K W. *Clin Ortho Rel Res* 1993; 295: 63-76), although in the case of infected non-unions or bony defects, this technology is typically used in two stage operations. In these cases, the defect or nonunion site is debrided as needed and the infection treated by placement of antibiotic-impregnated PMMA beads into the defect site. In the second stage, the beads are removed approximately six weeks later and a graft is used to repair the bone defect. The graft can be animal derived, allogenic, or autologous, such as COLLAGRAFT® bone graft matrix, demineralized bone matrix, or bone from the iliac crest, respectively. This two-stage methodology has also been widely adopted (Ueng S W N et al., *J Trauma* 1996; 40(3): 345-50; Ueng S W N et al., J Trauma 1997;43(2):268-74; Chen C Y et al., *J Trauma* 1997; 43(5): 793-8; Swiontkowski M F et al., *J Bone Joint Surg Br* 1999; 81(B6):1046-50).

In a logical progression of the technology, the two-stage method was soon followed by a one-stage procedure. In this technique, antibiotics are combined with the bone graft material in order to limit the intervention to a single surgery. Ideally, the resident antibiotic provides local delivery for prophylactic treatment of infection while the graft provides the environment to grow new bone. This methodology has also been widely adopted and used both with human autologous and bovine grafts as well as synthetic grafts (Chan Y S et al., *J Trauma* 1998; 45(4): 758-64; Chan Y S et al., *J Trauma: Inj Inf Crit Care* 2000; 48(2): 246-55; Winkler H et al., *J Antimicrobial Chemo* 2000; 46: 423-8; Sasaki S and Ishii Y., *J Ortho Sci* 1999; 4: 361-9; McKee M D et al., *J Ortho Trauma* 2002; 16(9): 622-7).

These approaches are not without their limitations. For example, the typical protocol for impregnation of antibiotic into PMMA is to heat the polymer to form a melt, then to mix powdered antibiotic into the liquid. The antibiotic must be heat stable to withstand the PMMA melt temperatures, which is often not the case so the number of potential antibiotics is limited. In addition, powdered antibiotic and liquid PMMA are not thermodynamically miscible; therefore the mixture is typically not homogeneous. This leads to uneven release of the antibiotic. Finally, the two-stage protocol subjects the patient to two surgeries and thereby, increased risk.

Similar limitations exist when impregnating graft materials with antibiotic. Typical graft materials are donor bone, demineralized bone matrix, or synthetic ceramic substitutes (e.g. hydroxyapatite), among others. These biomaterials are often not compatible with the antibiotic, and the resulting composite is non-homogeneous. Whether one employs impregnation into PMMA or a graft material, these methods, although clinically effective to some degree, are not controlled release systems and are by no means optimized for therapeutic dosing of antibiotics. They are osteoconductive, and in the case of autologous bone are certainly osteoinductive, but any approach that uses autologous bone subjects the patient to another wound. This increases risk to the patient and can lead to donor site morbidity, thereby compounding the original problem (Silber, J S et al., *Spine* 2003; 28(2): 134-9).

Obviously, healing bone defects is a challenging area of orthopaedic medicine. Current methods are not optimized for complete patient benefit. Ideally, bony defects should be healed with a graft material that provides both an osteoconductive and osteoinductive environment, and controlled, effective antibiotic treatment in a biomaterial that can be utilized in a single-stage operational protocol.

A recent review (Ludwig, S C et al., *Eur Spine J* 2000; 9(S1): S119-25) on the subject of bone graft substitutes listed the three most important elements of the ideal product as:

1. Osteoconductive in that it provides a scaffold conducive to vascular invasion, cell infiltration, and new bone formation;
2. Osteoinductive (i.e. capable of growth factor mediated differentiation of precursor cells into osteoblasts); and
3. Capable of delivering cells that will form new bone matrix.

Any effective regeneration scheme must seek to optimize all three of these parameters in order to recapitulate functional bone. Accordingly, there is a continuing need for new compositions useful as bone graft materials.

SUMMARY OF THE INVENTION

A first aspect of the invention is a malleable bone graft composition, comprising, consisting of or consisting essentially of:

(a) from 1 to 90 percent by weight keratose;
(b) from 1 to 90 percent by weight particulate filler (e.g., an osteoconductive filler);
(c) from 0.001 to 5 percent by weight antibiotic; and
(d) water to balance;

the composition having a viscosity of at least 3 centipoise at a temperature of 37° C.

in some embodiments the keratose is alpha keratose, gamma keratose, or mixtures thereof; in some embodiments the keratose is a mixture of alpha keratose and gamma keratose; in some embodiments the keratose comprises from 10 to 90 percent by weight alpha keratose and from 90 to 10 percent by weight gamma keratose; in some embodiments the said keratose is crosslinked keratose (e.g., produced by the process of combining the keratose with transglutaminase in the presence of a calcium initiator).

In some embodiments the composition further comprises from 0.001 to 5 percent by weight bone morphogenic protein.

In some embodiments the composition is sterile, and in some embodiments the composition is packaged in a sterile container.

A further aspect of the invention lyophilized or freeze-dried composition which upon reconstitution with water or saline solution produces a composition as described herein.

The foregoing and other objects and aspects of the present invention are explained in greater detail in the drawings herein and the specification set forth below. The disclosures of all United States patent references cited herein are to be incorporated by reference herein in their entirety.

DETAILED DESCRIPTION OF THE PREFERRED EMBODIMENTS

Figure 1A:
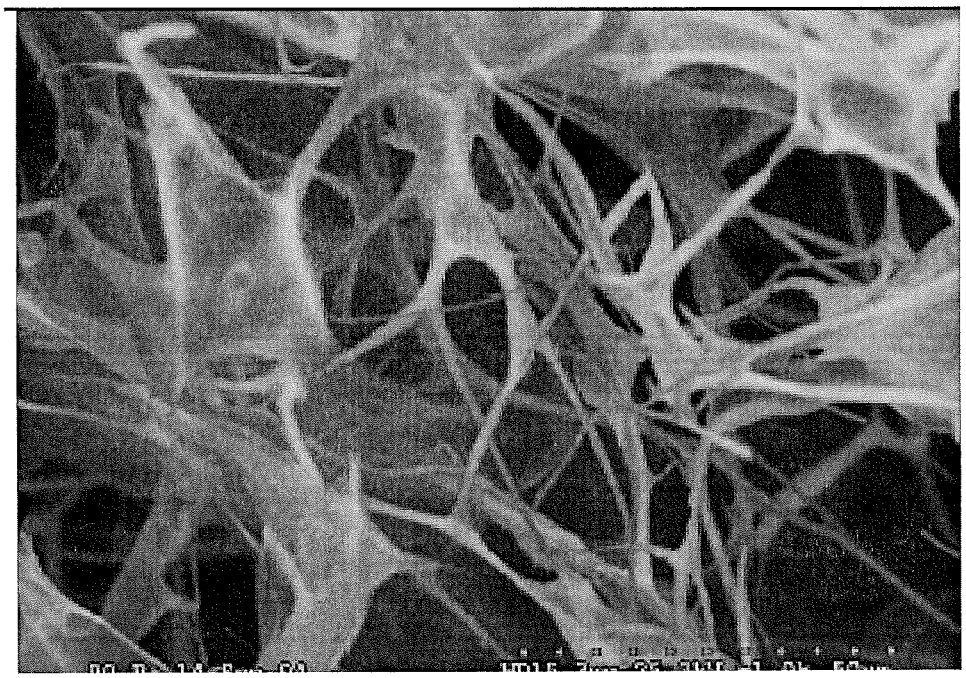
FIGS. 1A-1C Keratin biomaterial scaffold (1A) was formed spontaneously by a self-assembly mechanism. Notice the fibrous architecture, high porosity, and homogeneity similar to that of native ECM (1B; bladder submucosa ECM shown). This is in dramatic contrast to synthetic scaffolds that claim to have "interconnected" pores (1C). These types of synthetic scaffolds are difficult to seed at best and must rely on degradation of the matrix for tissue infiltration. This results in slower, less complete healing.
Figure 1B:
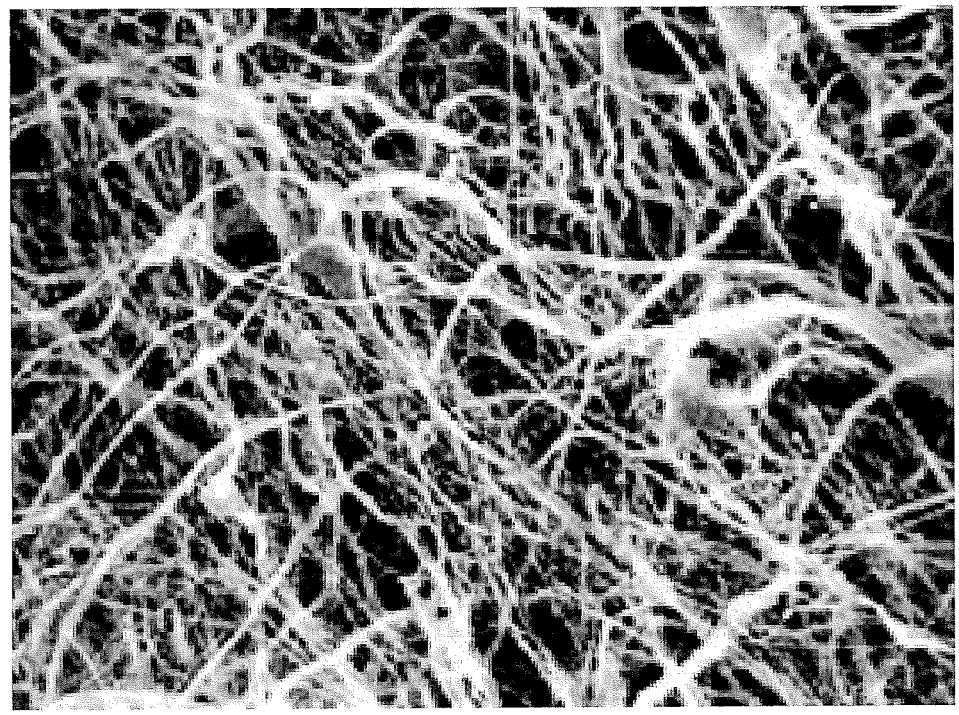
Figure 1C:
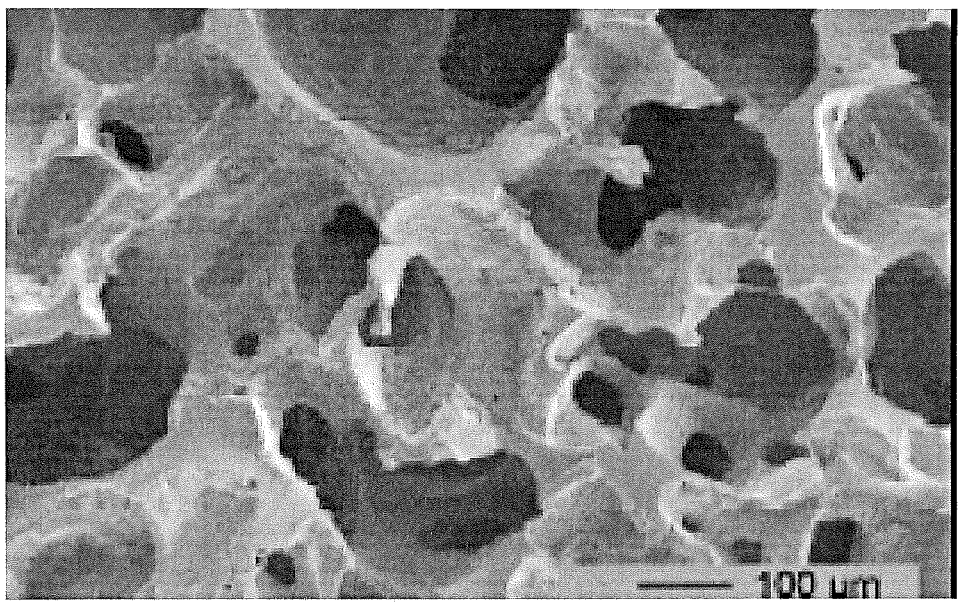

The compositions described herein are intended for use in the treatment of human subjects (including males and females, and including infant, juvenile, adolescent, adult and geriatric subjects) as well as animal subjects, particularly other mammalian subjects such as dogs, cats, horses, etc., for veterinary purposes.

"Bone" as used herein includes any bone, such as: the pelvis; long bones such as the tibia, fibia, femur, humerus, radius, and ulna, ribs, sternum, clavicle, etc.

"Fracture" or "break" as used herein with respect to bones includes any type thereof, including open or closed, simple or compound, comminuted fractures, and fractures of any location including diaphyseal and metaphyseal. "Fracture" as used herein is also intended to include defects such as holes, gaps, spaces or openings, whether naturally occurring or surgically induced (e.g., by surgical removal of undesired tissue from bone).

"Antibiotic" as used herein includes any suitable antibiotic, including but not limited to cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin and combinations thereof. See, e.g., U.S. Pat. No. 6,696,073. In some embodiments the antibiotic is preferably a water soluble antibiotic.

"Particulate fillers" used to carry out the present invention can be formed from any suitable biocompatible material, such as a ceramic. In some embodiments, the particulate filler is preferably osteoconductive. Examples of suitable materials from which the filler may be formed include but are not limited to tetracalcium phosphate, tricalcium phosphate, calcium alkali phosphate ceramic, calcium phosphorus apatite, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, collagen, allograft bone, other resorbable biocompatible materials and mixtures thereof. See, e.g., U.S. Pat. Nos. 6,869,445; 5,281,265. In some embodiments the particulate filler comprises hydroxyapatite, tricalcium phosphate, or a mixture thereof.

The particulate filler content of the composition of the present invention may be in a range from about 0.1 percent to about 200 percent of the keratin content of the composition. In some embodiments, the particulate filler content of the composition may be in a range from about 10 percent to about 100 percent of the keratin content. In other embodiments of the invention, the particulate filler content of the composition may be in a range from about 20 percent to about 90 percent of the keratin content. In further embodiments, the particulate filler content may be in a range from about 40 percent to 80 percent of the keratin content. In additional embodiments, the particulate filler content of the composition may be in a range from about 25 percent to about 50 percent of the keratin content. As an example, in one embodiment, when the keratin concentration in 100 g of gel is 20 percent (i.e., 20 g keratin per 80 g water) then the particulate filler content may be in a range from about 2 g to about 20 g.

In particular embodiments, the composition of the present invention has a consistency similar to toothpaste or modeling clay. Further, in representative embodiments, the viscosity of the composition is fluid and malleable and able to hold a form or shape without a supporting structure.

The composition of the present invention may be provided to the user in a dry form, which can be rehydrated for later use.

Keratin materials. Keratin materials are derived from any suitable source including but not limited to wool and human hair. In one embodiment keratin is derived from end-cut human hair, obtained from barbershops and salons. The material is washed in hot water and mild detergent, dried, and extracted with a nonpolar organic solvent (typically hexane or ether) to remove residual oil prior to use.

Scheme 1 below provides general representations of (a) oxidation and (b) reduction of disulfide crosslinks in keratin. These reactions cleave the sulfur-sulfur bond in cystine residues, thereby destroying the superstructure and rendering the keratins soluble in the reaction media.

Scheme 1.

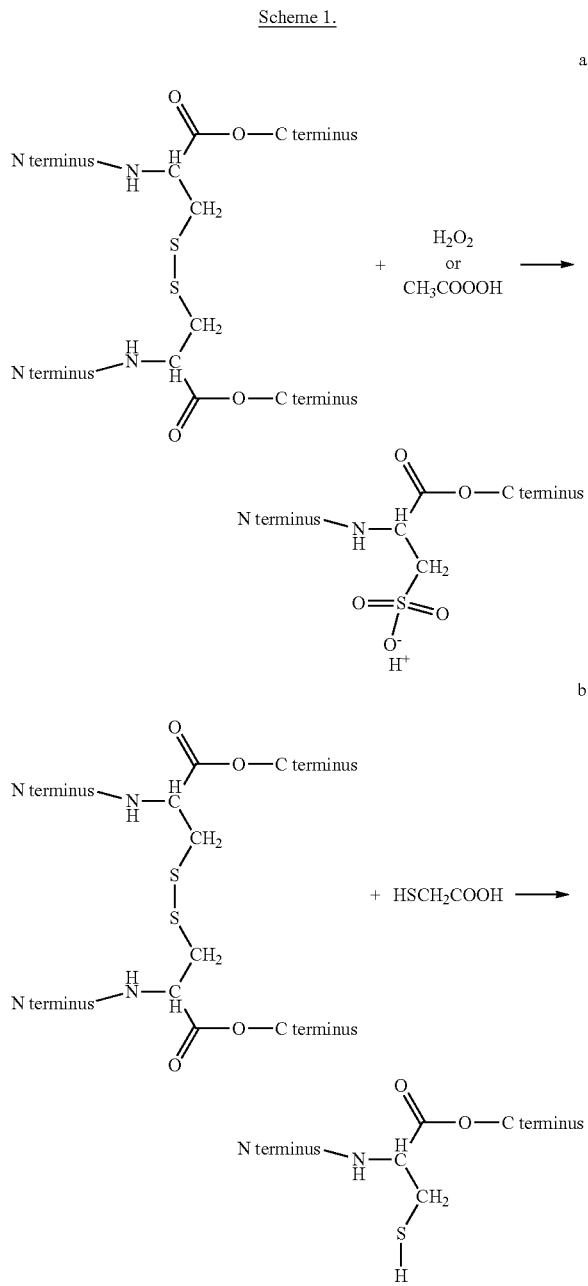

Keratose Fractions. Keratose fractions are obtained by any suitable technique. In one embodiment they are obtained using the method of Alexander and coworkers (P. Alexander et al., *Biochem. J.* 46, 27-32 (1950)). Basically, the hair is reacted with an aqueous solution of peracetic acid at concentrations of less than ten percent at room temperature for 24 hours. The solution is filtered and the alpha-keratose fraction precipitated by addition of mineral acid to a pH of ca. 4. The alpha-keratose is separated by filtration, washed with additional acid, followed by dehydration with alcohol, and then dried under vacuum. Increased purity can be achieved by redissolving the keratose in a denaturing solution such as 7M urea, aqueous ammonium hydroxide solution, or 20 mM tris base buffer solution, re-precipitating, re-dissolving, dialyzing against deionized water, and re-precipitating at pH 4.

The gamma-keratose fraction remains in solution at pH 4 and is isolated by addition to a water-miscible organic solvent such as alcohol, followed by filtration, dehydrated with additional alcohol, and dried under vacuum. Increased purity can be achieved by redissolving the keratose in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratose solution by distillation.

In use the compositions may be rehydrated if necessary, and used to treat fractures in a subject (e.g. filling bone defects) in accordance with known techniques by contacting the composition to the fracture in a treatment-effective amount. Fractures may be of any bone, including but not limited to: ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones, etc. Indeed the compositions may be used for any suitable purpose for which bone graft or osteogenic implants are used, as described in U.S. Pat. No. 6,863,694 to Boyce et al.

The present invention is explained in greater detail in the following non-limiting Examples.

Experimental

In this study, a keratin bioceramic antibiotic putty (KBAP) that provides osteoconductivity, osteoinductivity, and controlled antibiotic release is tested. The putty is comprised of a keratin hydrogel with ceramic filler and antibiotic. The KBAP is malleable and can be formed into shapes and pressed into a bony defect site with no additional preparation. It provides immediate and prophylactic antibiotic release as well as an osteoconductive and osteoinductive environment for bone regeneration in a single-stage operational protocol.

Keratin hydrogel is a proteinaceous network that is highly hydrated; therefore any water soluble antibiotics (e.g. Cefazolin, Gentamicin, and Vancomycin) can be used. The hydrophilicity of the hydrated keratin promotes cell attachment and in growth. The ceramic component may have the osteoconductive properties of products currently on the market (e.g., COLLAGRAFT®), but may not require aspirated bone marrow. The keratin matrix provides a highly biocompatible environment, as keratins are a class of proteins that elicit one of the lowest foreign body reactions among all biomaterials (Ito H et al., Kobunshi Ronbunshu 1982; 39(4):249-56; Blanchard C R et al., U.S. Pat. No. 6,461,628. Oct. 8, 2002; Tachibana A et al., J Biotech 2002;93:165-70).

When processed correctly, keratin proteins have a unique capability of molecular self-assembly, a process by which they reconstruct some semblance of their original tertiary structure (Sauk J J et al., J Cell Bio 1984;99:1590-7; Thomas H et al., Int J Biol Macromol 1986; 8:258-64; van de Löcht M. Melliand Textilberichte 1987; 10:780-6). This is a particularly useful characteristic for a bone graft substitute for two reasons. First, self-assembly results in a highly regular structure with reproducible architectures, dimensionality, and porosity. Second, the fact that these architectures form of their own accord under benign conditions allows for the incorporation of cells as the matrix is formed. These two features are critically important to any system that attempts to mimic the native ECM. The keratin scaffold shown in FIG. 1A was prepared by spontaneous self-assembly of a hydrogel and demonstrates the type of architecture conducive to cell infiltration and tissue regeneration.

Native ECM is a regular structure created around the cells, by the cells. In a tissue damage scenario, the ECM is an interactive medium for cell recruitment, growth, and differentiation, leading to the formation and maturation of new functional tissue. The ECM helps to orchestrate these processes by providing architectural support, growth factor delivery, and sites of molecular recognition whereby cells can bind and receive information.

Cellular recognition is facilitated by the binding of cell surface integrins to specific amino acid motifs of the ECM (Buck C A and Horwitz A F. Annu Rev Cell Biol 1987; 3:179-205; Akiyama S K. Hum Cell 1996; 9(3):181-6). The predominant ECM proteins are collagen and fibronectin, both of which have been extensively studied with regard to cell binding (McDonald J A and Mecham R P (editors). Receptors for extracellular matrix (1991). Academic Press, San Diego). Fibronectin contains several regions that support attachment by a wide variety of cell types. Mould et al. showed that in addition to the widely know Arginine-Glycine-Aspartic Acid (RGD) motif, the "X"-Aspartic Acid-"Y" motif on fibronectin is also recognized by the integrin $\alpha 4 \beta 1$ where X equals Glycine, Leucine, or Glutamic Acid and Y equals Serine or Valine (Mould A P et al., J Biol Chem 1991; 266(6):3579-85). Inexpensive, biocompatible scaffolds from keratin biomaterials contain these same binding motifs.

A recent search of the NCBI protein database revealed sequences for 71 discrete, unique human hair keratin proteins (Data from the National Center for Biotechnology Information (NCBI) database. http://www.ncbi.nlm.nih-.gov). Of these, 55 are from the high molecular weight, low sulfur, alpha-helical family. This group of proteins is often referred to as the alpha-keratins and is responsible for imparting toughness to human hair fibers. These alpha-keratins have molecular weights greater than 40 kDa and an average cysteine (the main amino acid responsible for inter- and intramolecular protein bonding) content of 4.8 mole percent. Importantly, analysis of the amino acid sequences of these alphakeratin proteins showed that 78% contain at least one fibronectin-like integrin receptor binding motif, and 25% contain at lease two or more. A recent paper has highlighted the fact that these binding sites are present on keratin biomaterials by demonstrating excellent cell adhesion to a keratin foam (Tachibana A et al., J Biotech 2002; 93:165-70). Although this paper uses fibroblasts to demonstrate the principle, the osteoconductivity of a keratin bioceramic was later demonstrated by these same authors (Tachibana A et al., Biomaterials 2005; 26(3):297-302).

Some studies are beginning to show mounting evidence that a number of growth factors are present in end-cut human hair, and that the keratins may be acting as a highly effective delivery matrix. It has been known for more than a decade that growth factors such as bone morphogenetic protein-4 (BMP-4) and other members of the transforming growth factor-$\beta$ (TGF-$\beta$) superfamily are present in developing hair follicles (Jones C M et al., *Development* 1991; 111: 531-42; Lyons K M et al., *Development* 1990; 109: 833-44; Blessings M et al., *Genes and Develop* 1993; 7: 204-15). 39-41 In fact, more than 30 growth factors and cytokines are involved in the growth of a cycling hair follicle (Stenn K S et al., *J Dermato Sci* 1994; 7S: S109-24). Many of these molecules have a pivotal role in the regeneration of a variety of tissues (Clark RAF (editor). *The molecular and cellular biology of wound repair* (1996) Plenum Press, New York). It is highly probable that a number of growth factors become entrained within human hair when cytokines bind to stem cells residing in the bulge region of the hair follicle (Panteleyev A A et al., *J Cell Sci* 2001; 114: 3419-31). We have recently analyzed extracts of human hair and shown the presence of growth factors such as vascular endothelial growth factor (VEGF) in these samples. We are currently assaying keratin biomaterials for the presence of several other growth factors including BMP, TGF-$\beta$, and nerve growth factor.

The preceding discussion demonstrates several key advantages that the KBAP has over conventional bone graft substitutes, and the ways in which we are leveraging our expertise to achieve the objective of developing a superior product. A keratin biomaterial with antibiotic filler provides sustained antibiotic release and has the potential to achieve this goal for the following reasons:

Keratin biomaterials are easily obtained and processed

Keratins are highly biocompatible

Keratins self-assemble into architectures that are conducive to cell attachment and growth Keratins contain sites of cellular recognition and are effective ECM surrogates Keratins are able to act as encapsulants or conjugates of drug compounds such as antibiotics and control their release kinetics Keratin biomaterials contain growth factors such as BMP that modulate cell growth and differentiation and therefore have the potential to impart osteoinductivity Results 1. Prepare a Bone Graft Putty Using a Keratin Matrix With a Mineral Component That can Incorporate Antibiotic Microcapsules.

There are many published methods that describe the extraction of keratins from hair fibers. In general, there are three procedures used to chemically break down the resilient structure of the hair fiber and impart aqueous solubility to the cortical keratin proteins of interest: 1) oxidation, 2) reduction, and 3) sulfitolysis (see, e.g., Crewther W G et al., Advances in protein chemistry (1965). Anfinsen C B Jr., Anson M L, Edsall J T, and Richards F M (editors). Academic Press. New York: 191-346; Goddard D R and Michaelis L., *J Bio Chem* 1934; 106: 605-14; Kelley R J et al., PCT Patent Application No. WO 03/011894; Zackroff R V and Goldman R D. *Proc Natl Acad Sci* 1979; 76(12): 6226-30). Efficient extraction depends first on breaking the disulfide bonds using one of these three methods, and second on gently denaturing the free proteins and affecting their dissolution. The importance of this second step cannot be over emphasized due to the existence of a competing reaction, hydrolysis of the peptide bonds in the keratin backbone. Hydrolysis of the protein backbone destroys many of the useful properties of keratins and must be avoided. We have evaluated all three of these methods as described more fully below, with the goal of creating a malleable putty that can be used to repair bony defects.

Figure 2:
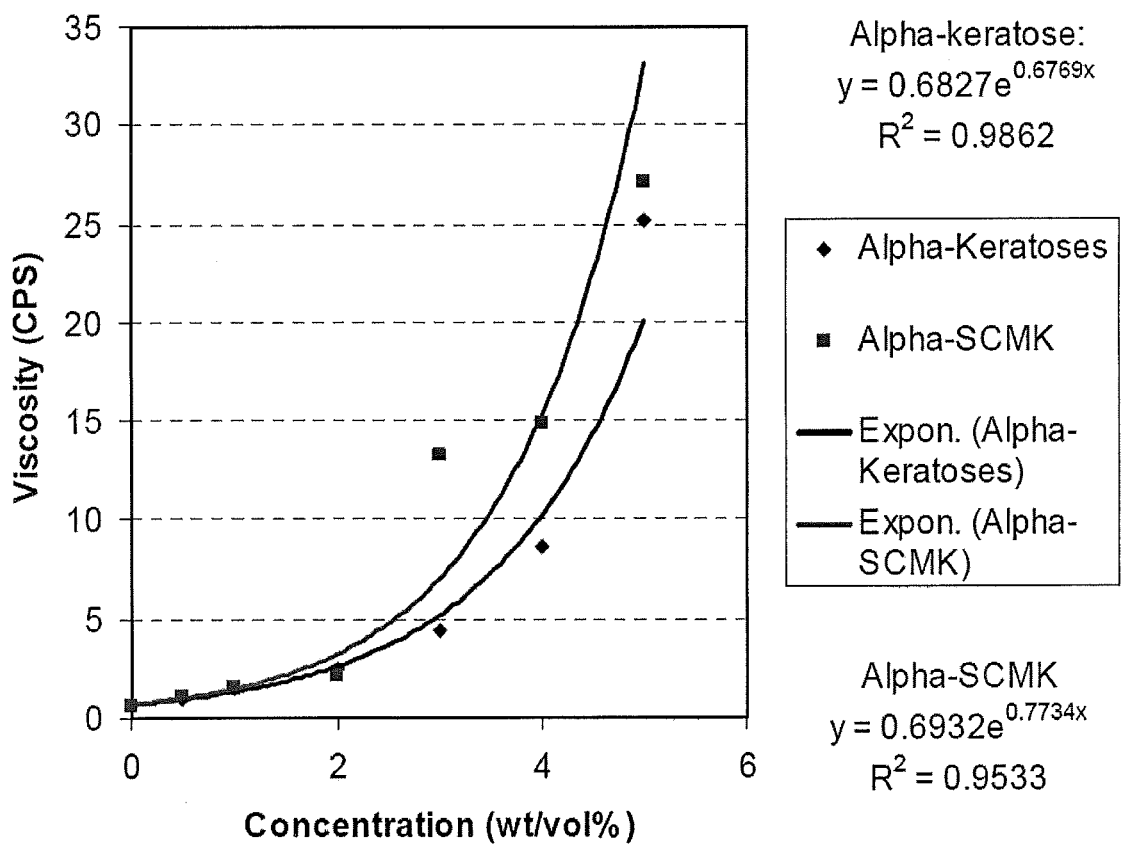
FIG. 2. Viscosity curves for α-keratose (bottom curve) and α-SCMK (top curve). Samples were formulated at 5 weight percent and below in RL solution to provide high porosity. Low solids content hydrogels are desired to provide biocompatibility and to accommodate the in growth of osteoblasts.

Oxidation: Human hair was obtained from a local salon, washed with mild detergent (Fisher Scientific, Pittsburgh, Pa.), degreased with ethyl ether (Sigma-Aldrich, St. Louis, Mo.), and dried in air. In a typical reaction, 20 grams of clean, dry hair was treated with 400 mL of a 2 weight/volume (w/v) % solution of peracetic acid (PAA, Sigma-Aldrich, St. Louis, Mo.) in deionized (DI) water. The oxidation was conducted in a closed polypropylene container maintained at 37° C. for 12 hours with gentle agitation. The oxidized hair was recovered and rinsed with copious amounts of DI water. The wet, oxidized hair was extracted with successive volumes of 0.2M tris base (Sigma-Aldrich, St. Louis, Mo.), 0.1M tris base, and DI water (500, 500, and 1000 mL, respectively). The extracts were combined and the α-keratose precipitated by drop wise addition of 12M hydrochloric acid (HCL; Fisher Scientific, Pittsburgh, Pa.) to a final pH of 4.2. The α-keratose was re-dissolved in 20 mM tris base with 20 mM ethylenediaminetetraacetic acid (EDTA; Sigma-Aldrich, St. Louis, Mo.), re-precipitated by drop wise addition of HCL to a final pH of 4.2, and again re-dissolved in tris base +EDTA. The resulting protein solution was dialyzed against DI water for three days with twice daily water changes (LMWCO 12.4K; Sigma-Aldrich, St. Louis, Mo.). After dialysis, the α-keratose powder was isolated by reducing the liquid volume via vacuum distillation at 50° C. and freeze-drying the concentrate. This sample was formulated at 5, 4, 3, 2, 1, and 0.5 weight percent in Ringer's lactate (RL) and analyzed for viscosity on a Brookfield cone and plate viscometer (Brookfield Engineering, Middleboro, Mass.) at 37° C. The viscosity data are shown in FIG. 2.

Reduction: A second sample of keratin was obtained using a different extraction protocol. Human hair was obtained from a local salon, washed with mild detergent, degreased with ethyl ether, and dried in air. In a typical reaction, 20 grams of clean, dry hair was treated with 400 mL of a 1.0M thioglycolic acid (Sigma-Aldrich) in DI water that had been titrated to pH 10.2 using saturated sodium hydroxide solution (Fisher Scientific). The reduction was conducted in a closed polypropylene container maintained at 37° C. for 12 hours with gentle agitation. The reduced hair was recovered and rinsed with copious amounts of DI water. The wet, reduced hair was extracted with three successive 500 mL volumes of 0.1M tris base with 0.1M thioglycolic acid. The extracts were combined and the α-kerateine precipitated by drop wise addition of 12M HCL to a final pH of 4.2. The α-kerateine was re-dissolved in 20 mM tris base with 20 mM EDTA, re-precipitated by drop wise addition of HCL to a final pH of 4.2, and again re-dissolved in tris base +EDTA. The protein solution was dialyzed against DI water for three days with twice daily water changes (LMWCO 12.4K). After dialysis, the α-kerateine was derivatized by reacting the cysteine residues with iodoacetic acid (Sigma-Aldrich) by adding 0.25 mg per mL of dialyzate. The reaction was performed in a closed polypropylene container maintained at 37° C., pH 9.0, with occasional stirring over 24 hours. Excess iodoacetic acid and other contaminants were removed by dialysis against DI water (LMWCO 12.4K). The dialyzate was concentrated by reduced pressure evaporation and the α-s-carboxymethylkerateine (α-SCMK) obtained by freeze-drying. Solutions of α-SCMK at 5, 4, 3, 2, 1, and 0.5 weight percent in RL were prepared and analyzed for viscosity as described previously. These data are also shown in FIG. 2.

Although these data trend toward acceptable viscosity values, formulating the hydrogels at 10 weight percent or less is desired to maintain biocompatibility and provide a porous matrix that can be populated by osteoblasts. Biomaterials with low porosity or pores that are too small (i.e. <85% and <100 μm, respectively) are difficult for cells to populate without first degrading them; this slows healing and can lead to fibrosis. The viscosities shown in FIG. 2 for formulations below 5% keratin were deemed to be unacceptably low. It was determined that the extraction conditions employed resulted in excessive hydrolysis, consequently, we modified our oxidation protocol to minimize this side reaction.

Oxidation (low hydrolysis method): In a typical procedure using this protocol, 50 grams of clean, dry hair was treated with 1,000 mL of a 2 weight/volume (w/v) % solution of PAA in DI water. The oxidation was conducted in a closed polypropylene container maintained at 37° C. for 12 hours with gentle agitation. The oxidized hair was recovered and rinsed with copious amounts of DI water. The wet, oxidized hair was extracted with 1,000 mL of 0.1M tris base and subsequently extracted with successive 1,000 mL volumes of DI water. The extracts were combined and concentrated 10-fold by reduced pressure evaporation at 50° C. The α-keratose was precipitated by drop wise addition of the concentrated solution to cold ethanol. The precipitate was re-dissolved in a minimum amount of DI water and re-precipitated by drop wise addition of 12M HCl to a final pH of 4.2. The α-keratose was isolated by centrifugation, re-dissolved in DI water, adjusted to a pH of 7.0, dialyzed against DI water for three days with twice daily water changes (LMWCO 12.4K), concentrated, and freeze dried. Solutions of the low hydrolysis (LH) α-keratose were prepared at 10 and 5 weight percent in phosphate buffered saline (PBS) and analyzed for viscosity as described previously. At 10 weight percent, the viscosity was too high to be measured by the viscometer. At 5 weight percent, the viscosity (analyzed at lower torque than previous measurements) was 460 centipoise at 37° C. From these data, we concluded that the LH method substantially reduced hydrolysis during keratin extraction and downstream processing.

Recognizing that additional improvements could potentially be made in our keratin production process, a small change was made to the LH extraction protocol described above. Rather than separate α- and γ-keratose by isoelectric precipitation, the crude extract was dialyzed to remove trace contaminants and residual processing chemicals, and the dialyzate concentrated and freeze dried. This results in a mixture of both α- and γ-keratose that has demonstrated improved viscoelastic properties. In addition, we attempted to improve the viscosity of the hydrogel formulation by crosslinking the keratose mixture. The details of this method are as follows: In a typical procedure, 50 grams of clean, dry hair was treated with 1,000 mL of a 2 weight/volume (w/v) % solution of PAA in DI water. The oxidation was conducted in a closed polypropylene container maintained at 37° C. for 12 hours with gentle agitation. The oxidized hair was recovered and rinsed with copious amounts of DI water. The wet, oxidized hair was extracted with 1,000 mL of 0.1M tris base and subsequently extracted with successive 1,000 mL volumes of DI water. The extracts were combined and concentrated 10-fold by reduced pressure evaporation at 50° C. The concentrated solution was dialyzed against DI water (LMWCO 12.4 K), concentrated, and freeze dried. 5 w/v % solutions of α+γ-keratose and α-keratose in DI water were prepared and their viscosities measured. These solutions were also reacted with a solution of transglutaminase (1 mg/mL; Sigma-Aldrich, St. Louis, Mo.) in an attempt to further increase their viscosity through glutamine-lysine crosslinking (both amino acids are prevalent in keratins). Interestingly, while the initial viscosity of the α+γ-keratose samples was lower than the α-keratose, the former achieved higher viscosity than the latter after only one hour of incubation at 37° C. Based on this observation, several formulations were prepared and crosslinked with transglutaminase, and the viscosities of the resulting gels measured. These data are shown in Table 1.

Figure 4:
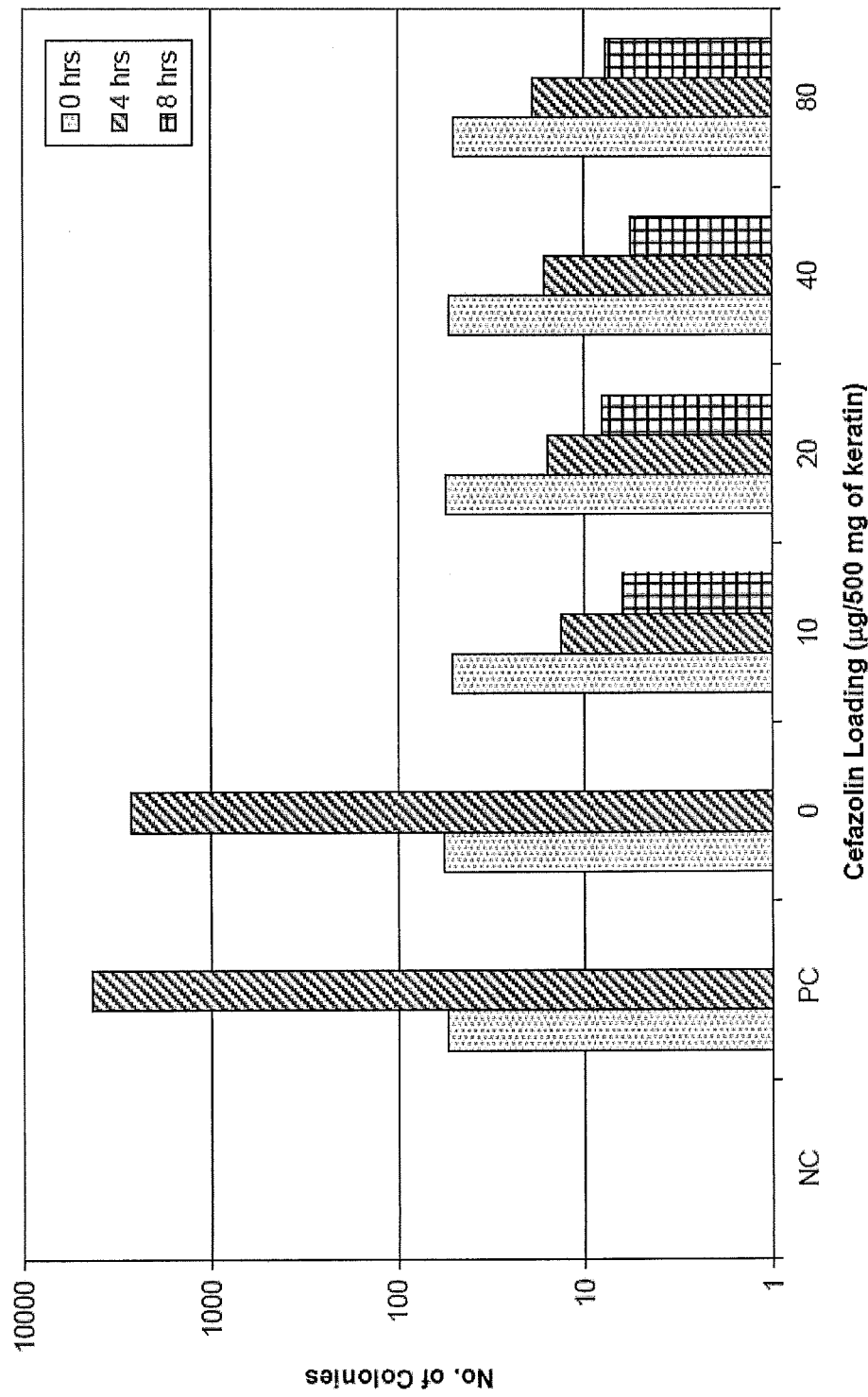
FIG. 4. Kill curves for an antibiotic containing keratin biomaterial. These data demonstrate the efficacy of a keratin biomaterial DDS on S. aureus. Effective arrest of the bacteria was noted at each concentration of Cefazolin.

These data must be interpreted carefully as the formulations contained less keratose than would normally be used for a KBAP formulation simply to ensure their viscosities were within the range of our equipment. Also, addition of the transglutaminase and a small amount of calcium initiator decreased the apparent weight percent keratose. These data suggest that in forming a high viscosity hydrogel a mixture of α+γ-keratose and the use of transglutaminase crosslinking may be useful. Qualitatively, the α-keratose solution decreased in viscosity after 1 hour of incubation at 37° C. while a similar α+γ-keratose solution increased. This phenomenon may be due to complex formation between the alpha and gamma forms of keratin.

formed into 500 mg disks using a manual press. The disks were used to generate kill curves for suspensions of *Staphylococcus aureus* ATCC 29213. Mueller Hinton broth cultures were prepared from an overnight sheep blood agar (SBA) culture of *S. aureus* so as to contain approximately 105 cfu per mL final concentration. Keratin disks were placed into culture tubes containing 2 mL final volume of *S. aureus* culture and incubated at 37° C. A 10 μL aliquot of each culture was removed at 0, 4, and 8 hours, diluted into 10 mL of saline, of which 100 μL were plated onto SBA using a glass spreader and inoculating turntable. Each concentration of antibiotic was tested in triplicate. The average number of colonies was calculated from the triplicate samples and compared to a positive control culture without antibiotic and a negative control culture without organisms. These data, shown in FIG. 4, demonstrate the efficacy of the keratin biomaterial DDS.

In a more recent experiment, a high viscosity KBAP formulation (LH method) was used to incorporate Cefazolin at 1000, 500, and 250 μg antibiotic by vortexing. The gel was cross-linked using 100 μl of 0.1% transglutaminase at 37° C. for 1 hour and the formulation was lyophilized to form a free standing disc. The Cefazolin release from the KBAP disk was measured in PBS using a modified Franz diffusion cell). The pellet (15 mg) was placed in the donor compartment, while the acceptor compartment was filled

TABLE 1

Viscosity of keratose formulations measured at 30 rpm and 37° C.

| No. | Type | Vol. of keratose solution used | Transglutaminase (vol. of 1 mg/mL solution) | Viscosity (cP) Initial | After 1 hr @ 37° C. |
|---|---|---|---|---|---|
| 1 | 1% α-keratose | 400 μL | 100 μL | 2.80 | 1.36 |
| 2 | 1% α-keratose | 300 μL | 300 μL | 2.80 | 1.23 |
| 3 | 1% α + γ-keratose | 400 μL | 200 μL | 1.71 | 2.24 |
| 4 | 1% α + γ-keratose | 300 μL | 200 μL | 1.71 | 2.69 |
| 5 | 2% α + γ-keratose | 300 μL | 0 μL | 2.43 | 1.86 |
| 6 | 2% α + γ-keratose | 300 μL | 200 μL | 2.43 | 1.93 |
| 7 | 5% α + γ-keratose | 800 μL | 100 μL | 5.72 | 3.72 |
| 8 | 5% α + γ-keratose | 800 μL | 200 μL | 5.72 | 3.08 |
| 9 | 5% α + γ-keratose | 700 μL | 200 μL | 5.72 | 2.65 |
| 10 | 5% α + γ-keratose | 700 μL | 400 μL | 5.72 | 3.03 |

Figure 3:
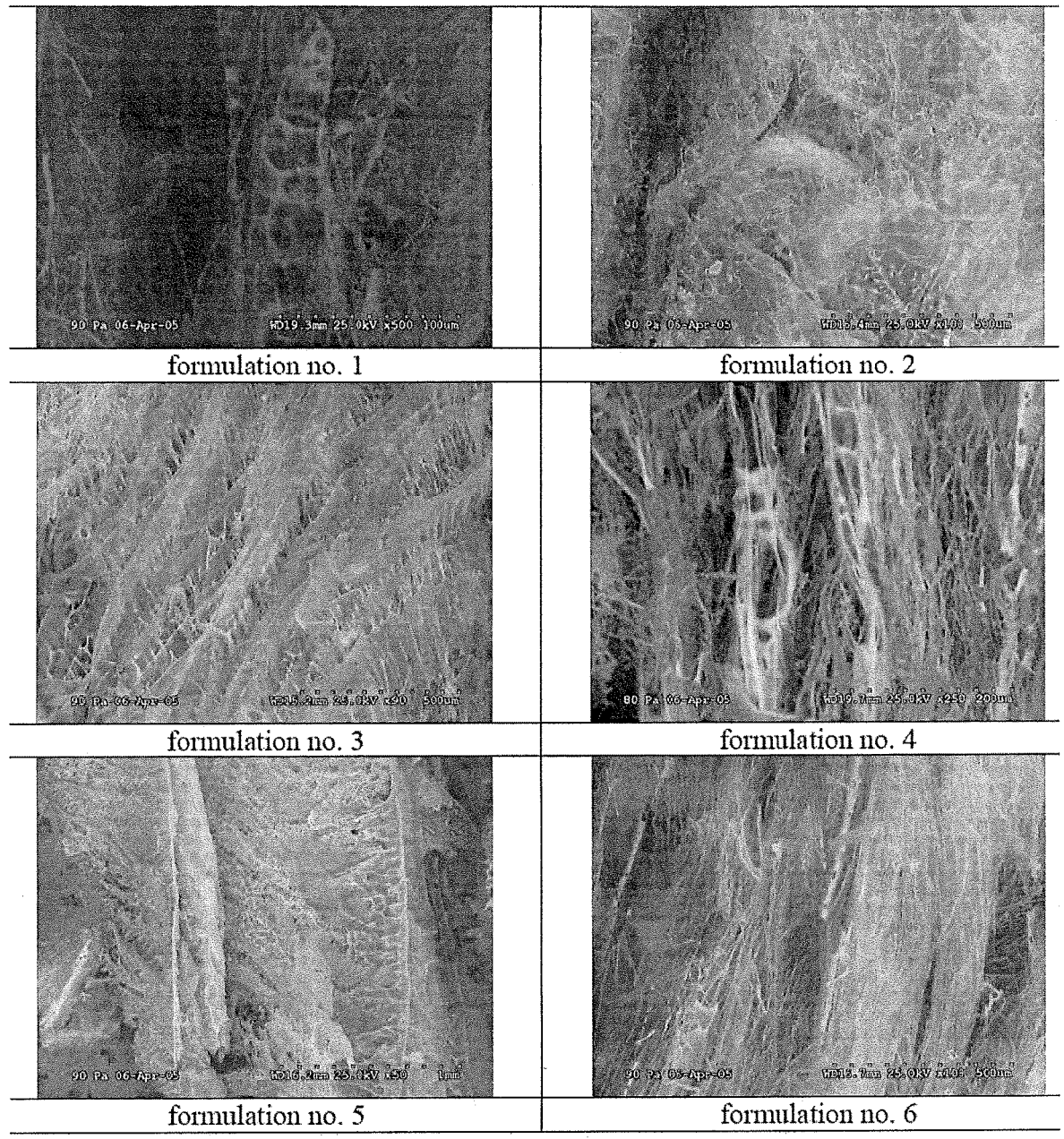
FIG. 3. SEM micrographs of keratose formulations (as defined in Table 1). Samples were created from lyophilized solutions in order to investigate the underlying microstructure of the hydrogels. Those gels showing the most fibrous microstructure also demonstrated the greatest increase in apparent viscosity.

In addition to viscosity analysis, the underlying microstructure of the first six of these gel formulations was investigated. Each formulation was recovered from the viscometer and freeze dried. The structures of the resulting samples were characterized by scanning electron microscopy (SEM; Model S-2600N; Hitachi High Technologies America, Inc., Pleasanton, Calif.) and are shown in FIG. 3. These images show the fibrous nature of the hydrogels and demonstrate the effect of this microstructure on viscosity. Formulation no. 4, for example, demonstrated one of the largest increases in viscosity after enzyme crosslinking; it also shows the most developed fibrous architecture. We believe the fibrous architecture is mediated by a process of molecular self-assembly, a unique characteristic of keratin-based biomaterials.

2. Optimize and Validate the Antibiotic Formulation

In order to demonstrate antibiotic delivery, we conducted an initial investigation using the keratin as a drug carrier. In these experiments, Cefazolin sodium was dissolved in aqueous α-kerateine solution at target concentrations of 0, 10, 20, 40, and 80 μg. The solutions were lyophilized and the solid samples ground into fine powders. The powders were with PBS. The donor compartment was separated from the acceptor compartment by a cellulose membrane (100 μm pore size). This diffusion cell was then placed in an incubator at 37° C. The solution in the acceptor compartment was periodically removed and replaced with and equal amount of fresh buffer solution. The Cefazolin released through the cellulose membrane was analyzed by UV/Vis spectrometry (Thermo Spectronic, USA, UV/VIS) at 285 nm.

Figure 5:
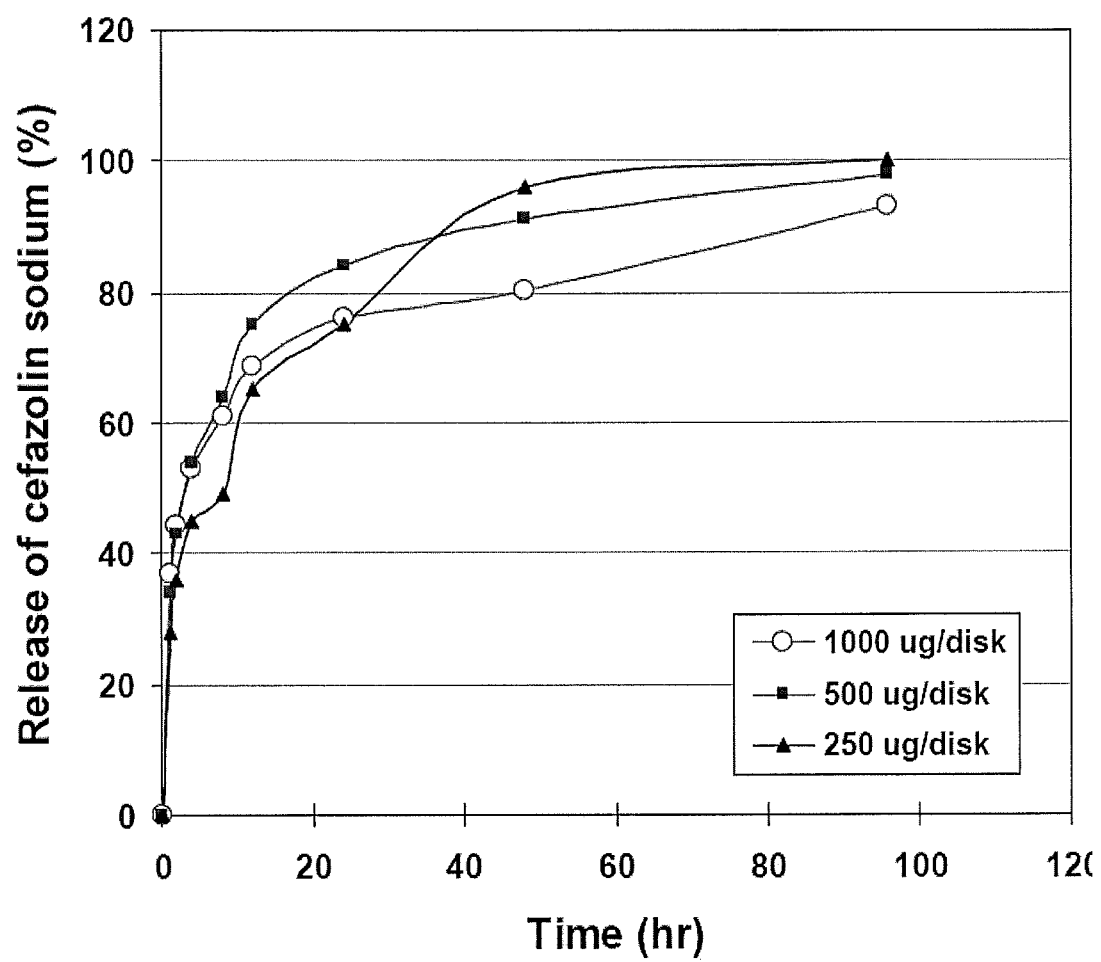
FIG. 5. Release kinetics for KBAP formulations containing Cefazolin were measured in a modified Franz diffusion cell (a). The antibiotic was simply added to the keratin hydrogel and was not encapsulated or chemically conjugated. Consequently, the release kinetics show rapid delivery in the first 24 hours, followed by much lower release during the subsequent 3 days. Encapsulation and conjugation methods are currently being developed to provide an MIC for up to 2 weeks.

As shown in FIG. 5, the release curves revealed a controlled release of Cefazolin from the KBAP formulation. Approximately 60~70% of the incorporated antibiotic was released from KBAP in one day and sustained the release for 4 days.

3. Biocompatibility, Osteoconductivity, and Osteoinductivity In Vitro.

Figure 6:
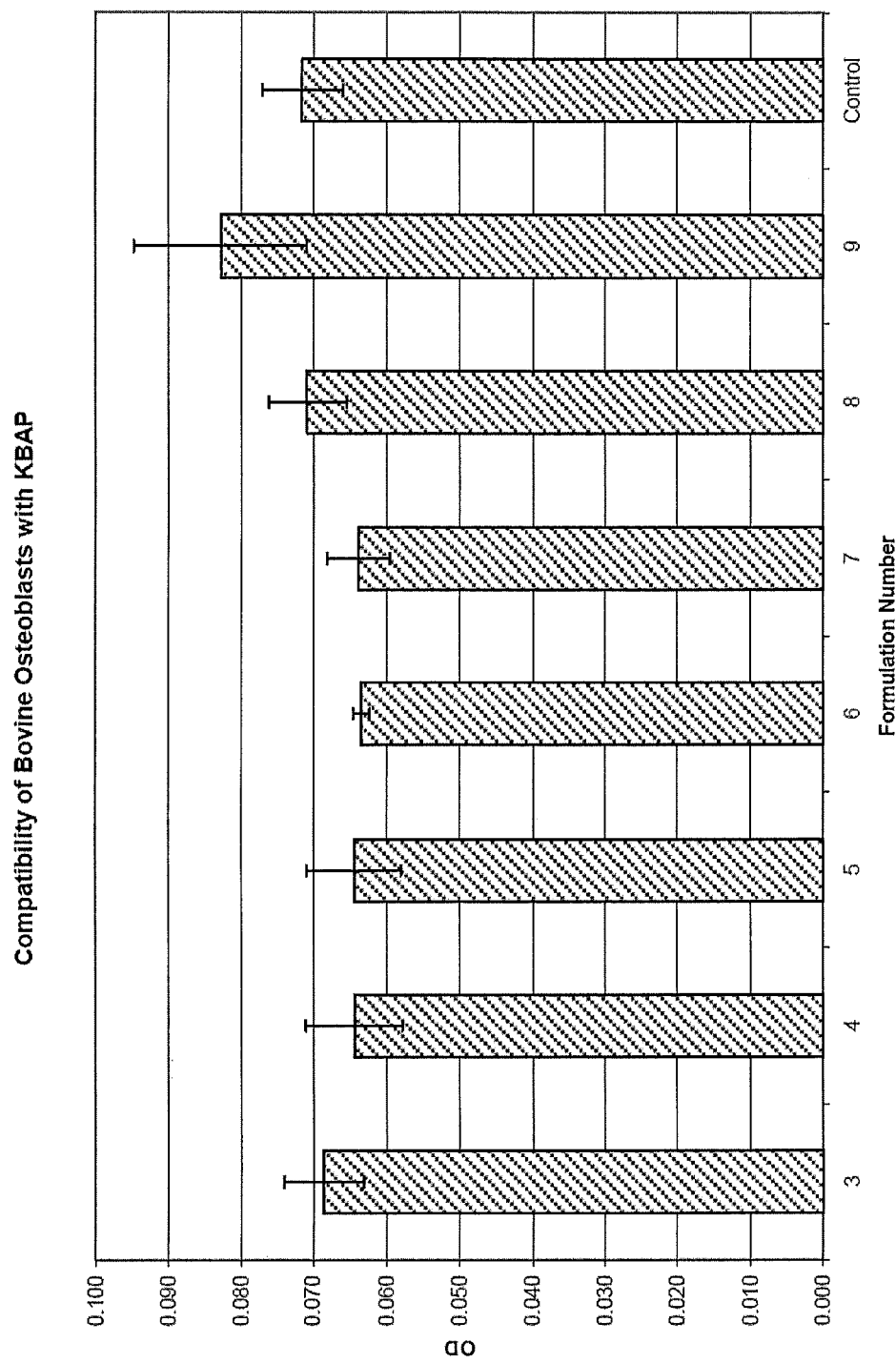
FIG. 6. Growth of bovine osteoblasts in the presence of six different KBAP formulations compared to control conditions (media alone). Optical density values (Y axis) are proportional to the total number of viable cells. These data suggest that KBAP formulation nos. 3, 4, 5, 8, and 9 are compatible with osteoblasts (p>0.05, n=5). Formulation nos. 6 and 7 reached near significance with p values of 0.030 and 0.041, respectively (n=5).

A sample of bovine osteoblasts was reconstituted from frozen stock by rapid thawing and plating onto a 10 cm tissue culture dish. The cells were cultured in 10 mL of low glucose DMEM containing 10% FBS (Invitrogen, Carlsbad, Calif.) with 0.05 mg/mL ascorbic acid (Sigma-Aldrich, St. Louis, Mo.) and antibiotics added. Media was changed three times per week and the cells were expanded by subculturing every 3-5 days. After at least three subculture cycles ("passages"), the cells were trypsinized and seeded in 96-well tissue culture plates at a density of approximately 3,000 cells per well. To each of five replicate wells was added approximately 1 mg of one of the KBAP formulations shown in Table 2. The KBAP had been lyophilized and gamma sterilized prior to placing in the media. After approximately 72 hours of incubation at 37° C., 5% CO2, and 95% humidity, 200 µL of 3-(4, 5-dimethylthiazolyl-2)-2,5-diphenyltetrazolium bromide (MTT; 1 mg/mL; Sigma-Aldrich, St. Louis, Mo.) was added to the culture wells, the cells were incubated for 4 hours, and the metabolic reduction product, MTT formazan, dissolved in a known amount of dimethylsulfoxide. The number of cells was measured indirectly by measuring the color intensity of metabolically reduced MTT using a microplate reader at 540 nm (model Elx800; Bio-Tek Instruments, Inc.; Winooski, Vt.). The optical density (OD) data from these cultures are shown in FIG. 6.

TABLE 2

KBAP formulations used in osteoconductivity testing

| No. | Cefazolin (mg) | Vol. of 10% α + γ-keratose gel used (µl) | Vol. of 5% chitosan lactate used (µL) | Vol. of 2% sodium alginate used (µL) | HA + TCP (mg) | Vol. of 0.5 mg/mL transglutaminase added (µL) | Vol. of 0.15% CaCl$_2$ used (µL) |
|---|---|---|---|---|---|---|---|
| 4 | 2 | 500 | 50 | 50 | 40 + 10 | 100 | 50 |
| 5 | 1 | 500 | 50 | 50 | 40 + 10 | 100 | 50 |
| 6 | 0 | 500 | 50 | 50 | 40 + 10 | 100 | 50 |
| 7 | 0 | 500 | 50 | 50 | 40 + 10 | 100 | 50 |
| 8 | 0 | 500 | 50 | 50 | 40 + 10 | 100 | 50 |
| 9 | 0 | 500 | 50 | 50 | 40 + 10 | 100 | 50 |

These data indicate that the KBAP formulations are capable of acting as osteoconductors as they will support the growth of osteoblasts in culture.

The ability of KBAP to recruit osteogenic cells through a chemotactic mechanism (i.e. osteoconduction) was assessed using a porous cell membrane insert. This technique determines the extent of cell migration through the porous membrane in response to a concentration gradient of chemotactic agent(s). In these experiments, KBAP was placed in serum free media at 37° C. and the supernatant removed at different time points such as 1, 3, 6, and 24 hours after immersion. This KBAP "extract" was placed in culture wells and the inserts place on top (not shown). Bovine osteoblasts were seeded at approximately $2\times10^4$ cells/well into the upper chamber and incubated at 37° C., 5% CO$_2$, and 95% relative humidity.

Cells cultured in the presence of serum free media alone was used as a control. After 6 and 20 hours of incubation, the membrane was fixed with glutaraldehyde and dehydrated with an alcohol gradient. The morphologic characteristics of the cells was examined by an environmental scanning electron microscopy (SEM; model N-2600 Hitachi, Japan).

Figure 7:
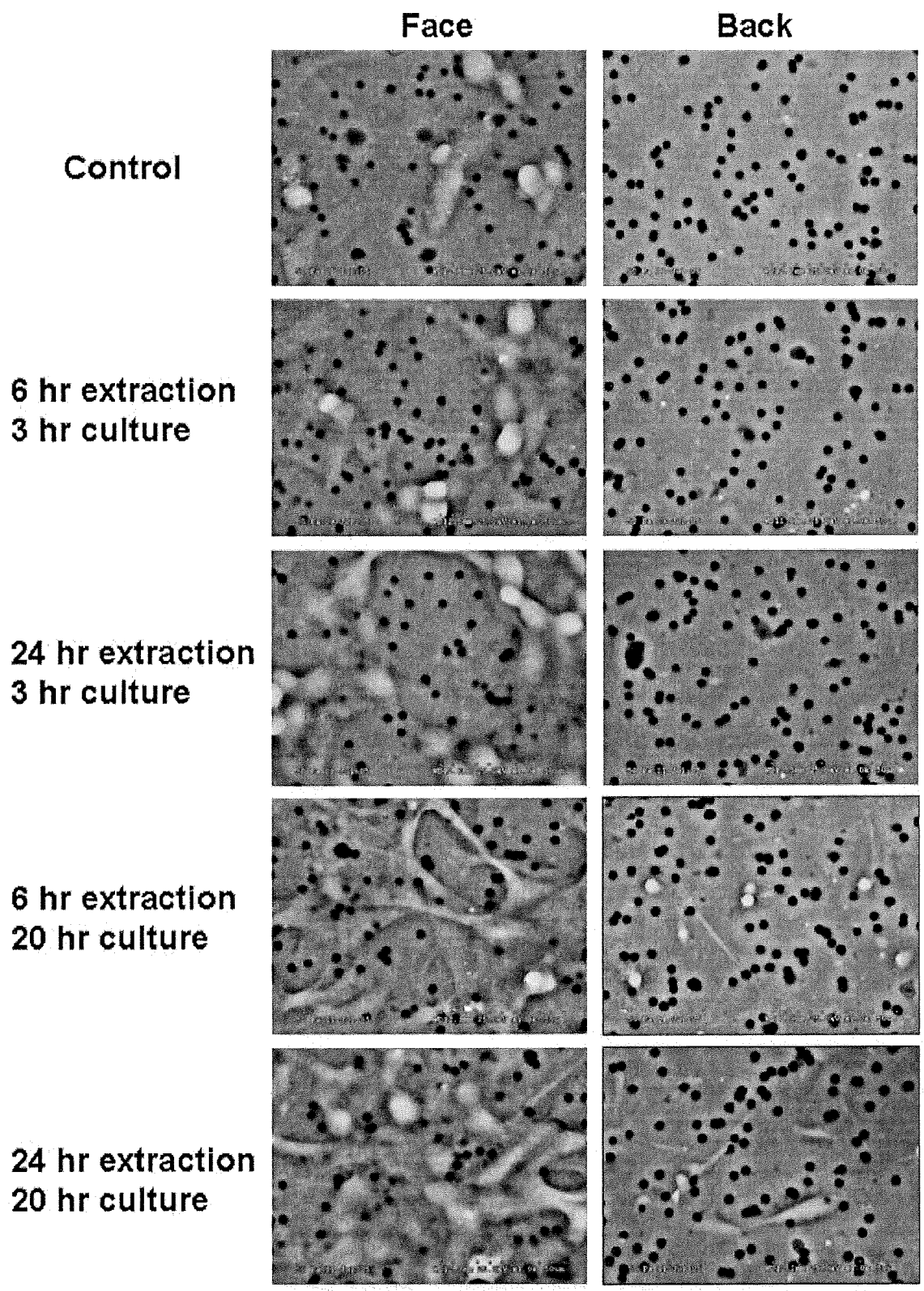
FIG. 7. Micrographs showing the effect of the KBAP extract on osteoblast migration.

The effect of the KBAP extract on osteoblast migration is apparent in the micrographs shown in FIG. 7. These data suggest that the KBAP possesses soluble molecules that are capable of affecting osteoblast migration. Media with no KBAP extract showed few cells on the top ("face") surface of the membrane and none on the bottom ("back"). Media that had been used to extract KBAP for 6 and 24 hours showed more cells on the top surface, with 24 hours of extracting appearing to be slightly more effective. More importantly, cells migrated through the pores to the bottom surface of the membrane in the presence of KBAP extract after 20 hours of culture. These data indicate the chemotactic potential of KBAP's soluble fraction and the latent osteoinductivity of keratin biomaterials.

4. Conclusions. We evaluated three forms of keratin biomaterials for suitability in a bone graft substitute formulation termed keratin bioceramic antibiotic putty or KBAP. A low hydrolysis method for the extraction of keratins from human hair fibers was developed such that the protein possessed the desired viscoelastic characteristics. We discovered that when high molecular weight keratins were obtained, they were capable of self-assembling into fibrous micro-architectures that are conducive to cell infiltration and growth.

We further improved the physical characteristics of this self-assembled hydrogel by crosslinking strategies. From this keratin-based hydrogel, we developed a malleable KBAP prototype formulation that contained a drug delivery system capable of releasing antibiotics.

The KBAP prototype formulation was tested for antibiotic release in an in vitro model using *S. aureus* and was shown to effectively kill this species of bacteria. We further characterized the antibiotic release by determining the in vitro release kinetics. The biocompatibility of several different KBAP formulations was demonstrated in vitro using bovine osteoblasts, and the osteoinductivity of human hair keratins was shown using a cell migration assay. These data show the feasibility of formulating a malleable bone graft substitute with antibiotic release from a keratin biomaterial.

The foregoing is illustrative of the present invention, and is not to be construed as limiting thereof. The invention is defined by the following claims, with equivalents of the claims to be included therein.

That which is claimed is:

1. A method of treating a fracture in a subject in need thereof, comprising contacting to said fracture in a treatment-effective amount: a malleable bone graft composition, comprising:
   (a) from 5 to 30 percent by weight keratose, wherein the keratose is present in the composition as a keratose hydrogel;
   (b) from 1 to 30 percent by weight particulate filler;
   (c) from 0.001 to 5 percent by weight antibiotic; and
   (d) water to attain 100 percent by weight,
wherein a ratio of the particulate filler to the keratose is from 0.1:1 to 1:1.

2. The method of claim 1, wherein said keratose comprises a mixture of alpha keratose and gamma keratose.

3. The method of claim 2, wherein said keratose comprises from 10 to 90 percent by weight of the alpha keratose and from 90 to 10 percent by weight of the gamma keratose.

4. The method of claim 1, wherein said keratose hydrogel comprises crosslinked keratose.

5. The method of claim 4, wherein said crosslinked keratose is produced by the process of combining said keratose with transglutaminase in the presence of a calcium initiator.

6. The method of claim 1, wherein the composition further comprises from 0.001 to 5 percent by weight bone morphogenic protein.

7. The method of claim 1, wherein said particulate filler is osteoconductive.

8. The method of claim 1, wherein said particulate filler is selected from the group consisting of tetracalcium phosphate, tricalcium phosphate, calcium alkali phosphate ceramic, bioglass, calcium carbonate, calcium hydroxide, calcium oxide, calcium fluoride, calcium sulfate, magnesium hydroxide, hydroxyapatite, calcium phosphorus apatite, magnesium oxide, magnesium carbonate, magnesium fluoride, collagen, and mixtures thereof.

9. The method of claim 1, wherein said particulate filler comprises hydroxyapatite, tricalcium phosphate, or a mixture thereof.

10. The method of claim 1, wherein said antibiotic is selected from the group consisting of cefazolin, vancomycin, gentamycin, erythromycin, bacitracin, neomycin, penicillin, polymycin B, tetracycline, biomycin, chloromycetin, streptomycin, ampicillin, azactam, tobramycin, clindamycin, gentamicin and combinations thereof.

11. The method of claim 1, wherein said composition is sterile.

12. The method of claim 1, further comprising a step of reconstituting a lyophilized or freeze-dried composition comprising the keratose, particulate filler, and antibiotic with water or saline solution to produce said malleable bone graft composition prior to said contacting step.

13. The method of claim 1, wherein said composition comprises from 5 to 20 percent by weight of said keratose.

14. The method of claim 1, wherein said composition comprises from 7 to 20 percent by weight of said keratose.

15. The method of claim 1, wherein said composition comprises from 5 to 10 percent by weight of said keratose.

16. The method of claim 1, wherein said composition comprises from 7 to 10 percent by weight of said keratose.

17. The method of claim 1, wherein said composition is a putty comprising a matrix of the keratose hydrogel.

\* \* \* \* \*